US006355490B1

(12) United States Patent
Hochlowski et al.

(10) Patent No.: US 6,355,490 B1
(45) Date of Patent: *Mar. 12, 2002

(54) ATTACHED TAGS FOR USE IN COMBINATORIAL CHEMISTRY SYNTHESIS

(76) Inventors: Jill Edie Hochlowski, 31165 O'Plaine Rd., Green Oaks, IL (US) 60048; Thomas J. Sowin, 40338 Reed Ct., Wadsworth, IL (US) 60083; Daniel W. Norbeck, 2810 Federal Ct., Crystal Lake, IL (US) 60012; Anne-Laure Marie Grillot, 99 Hammond St. Apt. #2, Cambridge, IL (US) 60093; Rolf E. Swenson, 285 Penny La., Grayslake, IL (US) 60030

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/923,206

(22) Filed: Sep. 4, 1997

Related U.S. Application Data

(63) Continuation-in-part of application No. 08/713,710, filed on Sep. 13, 1996, now abandoned.

(51) Int. Cl.[7] .................... G01N 33/543; G01N 33/552; C07C 255/00
(52) U.S. Cl. .................. 436/518; 436/527; 436/528; 436/531; 436/56; 530/333; 530/334; 530/335; 558/303; 558/411; 558/415; 558/416; 558/414; 558/435; 558/441
(58) Field of Search .................. 435/7.1, 7.9, DIG. 1, 435/DIG. 40, DIG. 41, DIG. 49; 436/518, 56, 527, 528, 531; 250/339.11, 341.8, 339.14; 558/303, 411, 415, 416, 414, 435, 441; 530/333, 334, 335

(56) References Cited

U.S. PATENT DOCUMENTS 5,565,324 A * 10/1996 Still et al. .................. 435/6
5,708,153 A    1/1998 Dower et al.
5,786,218 A * 7/1998 Pivonka et al. ............ 436/34

FOREIGN PATENT DOCUMENTS

GB    2304410    3/1997
WO    9408051    4/1994

OTHER PUBLICATIONS

B. Yan et al., "Infrared Spectrum of a Single Resin Bead for Real–Time Monitoring of Solid–Phase Reactions", *J. Org. Chem.*, vol. 60, No. 17, (1995), pp. 5736–5738.
C. Chen et al., "'Analogous' organic Synthesis of Small–Compound Libraries: Validation of Combinatorial Chemistry in Small–Molecule Synthesis", *J. Am. Chem. Soc.*, vol. 116, No. 6, (1994), pp. 2661–2662.

H. M. Geysen et al., "Isotope or Mass Encoding of Combinatorial Libraries", *Chemistry and Biology*, vol. 3, No. 8, (1996), pp. 679–688.
S. Brenner et al., "Encoded Combinatorial Chemistry", *Proc. Natl. Acad. Sci. USA*, vol. 89, (1992), pp. 5381–5383.
V. Nikolaiev et al., "Peptide–Encoding for Structure Determination of Nonsequenceable Polymers Within Libraries Synthesized and Tested on Solid–Phase Supports", *Peptide Research*, vol. 6, No. 3, (1993), pp. 161–170.
R. W. Armstrong et al., "Microchip Encoded Combinatorial Libraries: Generation of a Spatially Encoded Library from a Pool Synthesis", *Medicinal Chemistry*, vol. 50, No. 6, (1996), pp. 258–260.
A. Furka et al., "General Method for Rapid Synthesis of Multicomponent Peptide Mixtures", *Int. J. Peptide Res.*, vol. 37, (1991), pp. 487–493.
K. Russell et al., "Analytical Techniques for Combinatorial Chemistry: Quantitative Infrared Spectroscopic Measurements of Deuterium–Labeled Protecting Groups", *J. Am. Chem.*, vol. 118, (1996), pp. 7941–7945.
M. H. J. Ohlmeyer et al., "Complex Synthetic Chemical Libraries Indexed with Molecular Tags", *Proc. Natl. Acad. Sci. USA*, vol. 90, (1993), pp. 10922–10926.
E. J. Moran et al., "Radio Frequency Tag Encoded Combinatorial Library Method for the Discovery of Tripeptide–Substituted Cinnamic Acid Inhibitors of the Protein Tyrosine Phosphatase PTP1B", *J. Am. Chem. Soc.*, vol. 117, No. 43, (1995), pp. 10787–10788.
Z. J. Ni et al., "Versatile Approach to Encoding Combinatorial Organic Syntheses Using Chemically Robust Secondary Amine Tags", *J. Med. Chem.*, vol. 39, (1996), pp. 1601–1608.
A. Borchardt et al., "Synthetic Receptor Binding Elucidated with an Encoded Combinatorial Library", *J. Am. Chem. Soc.*, vol. 116, (1994), pp. 373–374.
J. J. Baldwin et al., "Synthesis of a Small Molecule Combinatorial Library Encoded with Molecular Tags", *J. Am. Chem. Soc.*, vol. 117, (1995), pp. 5588–5589.
J. M. Kerr et al., "Encoded Combinatorial Peptide Libraries Containing Non–Natural Amino Acids", *J. Am. Chem. Soc.*, vol. 115, (1993), pp. 2529–2531.
H. P. Nestler et al., "A General Method for Molecular Tagging of Encoded Combinatorial Chemistry Libraries", *J. Org. Chem.*, vol. 59, No. 17, (1994), pp. 4723–4724.
K. C. Nicolaou et al., "Radiofrequency Encoded Combinatorial Chemistry", *Angew. Chem. Int. Ed. Engl.*, vol. 34, No. 20, (1995), pp. 2289–2291.3q.

* cited by examiner

Primary Examiner—Padmashri Ponnaluri
(74) Attorney, Agent, or Firm—Daniel W. Collins

(57) ABSTRACT

The present invention relates to a process of coding and identifying individual members of a chemical combinatorial library synthesized on a plurality of solid supports which undergo mix and split synthesis. The process provides for tagging the solid supports with a coding identifier that is attached to the solid support and which can be decoded by infrared or raman spectroscopy when directly attached to the support.

4 Claims, 19 Drawing Sheets

ATTACHED TAGS FOR USE IN COMBINATORIAL CHEMISTRY SYNTHESIS

CROSS-REFERENCE TO RELATED APPLICATION

This is a continuation-in-part of U.S. patent application Ser. No. 08/713,710, now abandoned filed on Sep. 13, 1996.

TECHNICAL FIELD OF THE INVENTION

The present invention relates to a process of coding and identifying individual members of a chemical combinatorial library synthesized on a plurality of solid supports. The process provides for tagging the solid supports with a coding identifier that is decoded while attached to the solid support by infrared or Raman spectroscopy.

BACKGROUND OF THE INVENTION

Typically, methods for the synthesis of large numbers of diverse compounds involve successive chemical modifications of existing molecules. Modifications can include the addition of a chemical unit to a growing sequence or modification of a functional group. Chemical units can take many forms, both naturally-occurring and synthetic, including compounds containing reactive functional groups such as neculeophiles, electrophiles, dienes, alkylating agents, acylating agents, diamines, nucleotides, amino acids, sugars, lipids or derivatives thereof, organic monomers, synthons, and combinations thereof. Alternatively, reactions can be involved which result in alkylation, acylation, nitration, halogenation, oxidation, reduction, hydrolysis, substitution, elimination, addition, and the like. This process can produce non-oligomers, oligomers, or combinations thereof in extremely small amounts, where the reaction history, and composition in appropriate cases, can be defined by the present tags. Non-oligomers include a wide variety of organic molecules, e.g., heterocyclics, aromatics, alicyclics, aliphatics and combinations thereof, such as steroids, antibiotics, enzyme inhibitors, ligands, hormones, drugs, alkaloids, opioids, terpenes, porphyrins, toxins, catalysts, as well as combinations thereof. Oligomers include oligopeptides, oligonucleotides, oligosaccharides, polylipids, polyesters, polyamides, polyurethanes, polyethers, poly (phosphorus derivatives) e.g., phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom for the most part will be bonded to C, H, N, O and combinations thereof.

Reactions can involve modifications at a variety of random sites of a central core molecular structure or modifications at specific sites. For example, one can brominate a polycyclic compound, where bromination can occur at a plurality of sites or use a brominating agent which will be specific for a particular site, e.g., N-bromosuccinimide. Typically, reactions will involve single sites or equivalent sites, for example, one of two hydroxyl groups of a glycol. For the most part, the subject synthesis will have at least two stages where other than bifunctional compounds are attached using the same linking functionality, e.g., amino acids and amide bonds, nucleotides and phosphate ester bonds, or mimetic compounds thereof, e.g., aminoisocyanates and urea bonds.

The synthetic strategies will vary with the nature of the group of products one wishes to produce. Thus, the strategy must take into consideration the ability to change the nature of the product, while allowing for retention of the results of the previous stages and anticipating needs for the future stages. Where the various units are of the same family, such as nucleotides, amino acids and sugars, the synthetic strategies are relatively well-established and frequently conventional chemistry will be available. Thus, for nucleotides, phosphoramidite or phosphite chemistries can be employed; for oligopeptides, fluorenylmethyl (Fmoc), t-butyoxycarbonyl (Boc), etc. protection chemistries can be employed; for sugars, the strategies can be less conventional but a large number of protective groups, reactive functionalities, and conditions have been established for the synthesis of polysaccharides. For other types of chemistries, one will look to the nature of the individual unit and either synthetic opportunities will be known or will be devised, as appropriate.

Techniques have recently been developed wherein individual units are added sequentially in a controlled or random manner to produce all or a substantial proportion of possible compounds resulting from the different choices possible at each sequential stage in the synthesis. One disadvantage is that individual compounds are present only in minute amounts. While the biological activity of a given compound can be determined, the chemical structure of that particular compound cannot necessairly be determined. It is necessary for compounds made by such techniques to be amenable to methods for determining their composition.

There is a substantial interest in discovering methods for producing compounds which are not limited to sequential addition of like moieties, but frequently involve a multistage synthesis in which the reagents and/or conditions are varied to provide a variety of compounds. There needs to be, however, convenient ways to identify the structures of the large number of compounds which result from a wide variety of different modifications. Thus, there is a need to record the reaction history or the structures of the compound identified.

As the size of compound libraries increases, existing means for elucidating structure and segregating products introduce substantial inefficiencies and uncertainties that hinder accurate structure determination. Thus, there is a substantial need for new methods which will permit the synthesis of complex combinatorial chemical libraries, which readily permit accurate structural determination of individual compounds within the library which are identified as being of interest.

BRIEF DESCRIPTION OF THE INVENTION

The present invention provides a process of coding individual members of a combinatorial chemistry library using attached Infrared or Raman chromophores. The process provides for the partial or complete identification of a library member compound or the synthetic pathway generating that compound on any solid support.

The solid support is uniquely tagged to define a particular event, usually chemical, associated with the synthesis of the compound on the support using coding identifier molecules that record the sequential events to which the supporting particle is exposed during synthesis, thus providing a reaction history for the compound produced on the support.

Each coding identifier is stable under the synthetic conditions employed, remains associated with the support during the stage of the synthesis, assay, and library cleavage, uniquely defines a particular event during the synthesis that reflects a particular reaction choice at a given stage of the synthesis, and is distinguishable from other components that can be present during assaying. The coding identifier is covalently attached to the solid support.

By associating each stage or combination of stages (e.g., "add reagent A" or "add reagent A, then reagent B, and heat to 100° C. for 2 hours") of the serial synthesis with an identifier which defines the choice of variables such as reactant, reagent, reaction conditions, or a combination of these, one can use the identifiers to define the reaction history of each definable and separable substrate. The spectrophotometric analysis of identifiers allows for ready identification of the reaction history, at picomolar or lower concentrations. One can determine a characteristic of a product of a synthesis, usually a chemical or biological characteristic by various screening techniques, and then identify the reaction history and thereby the structure of that product, which has the desired characteristic, by virtue of the tag(s) associated with the product.

An advantage of the present invention lies in the fact that the code can be read directly on the bead, thus expanding the scope of chemistry compatible with the tag as well as the scope of assay capabilities: the tag(s) remains with the bead during partial or complete release of the library entity.

The use of the instant multiple tag system avoids the necessity of carrying out a complicated cosynthesis which reduces yields and requires multiple protecting groups and avoids the necessity of using sequential (e.g., nucleic acid or peptide oligomers) tags which are necessarily chemically labile. Both the necessity of multiple protecting groups and the intrinsic instability of all known sequential tagging molecules severely limit the chemistry which can be used in the synthesis of the library element or ligand.

The coding identifiers of this invention are used in combination with one another to form a binary or higher order encoding system permitting a relatively small number of identifiers to be used to encode a relatively large number of reaction products. For example, N identifiers can uniquely encode up to $2^N$ different compounds in a binary code. Thus, 30 distinguishable tags are available and are sufficient to encode >$10^9$ different syntheses. A ternary coding system could encode for this same number with significantly less than 30 distinguishable tags.

Moreover, the use of a binary, or higher, multiple tag system reduces enormously the number of tags necessary to encode the reagent/reactant choice in any stage in a synthesis. For example, if a particular synthetic stage could be carried with 125 different choices for reagent, the binary system would require only 7 tags. Further, ternary coding would accomplish this with substantially less tags. This can make the difference between a practical encoding system and an impractical one, because it may not be feasible to obtain and use the large number of distinguishable tags required by other systems.

DETAILED DESCRIPTION OF THE INVENTION

A. Definition of Terms

Figure 1:
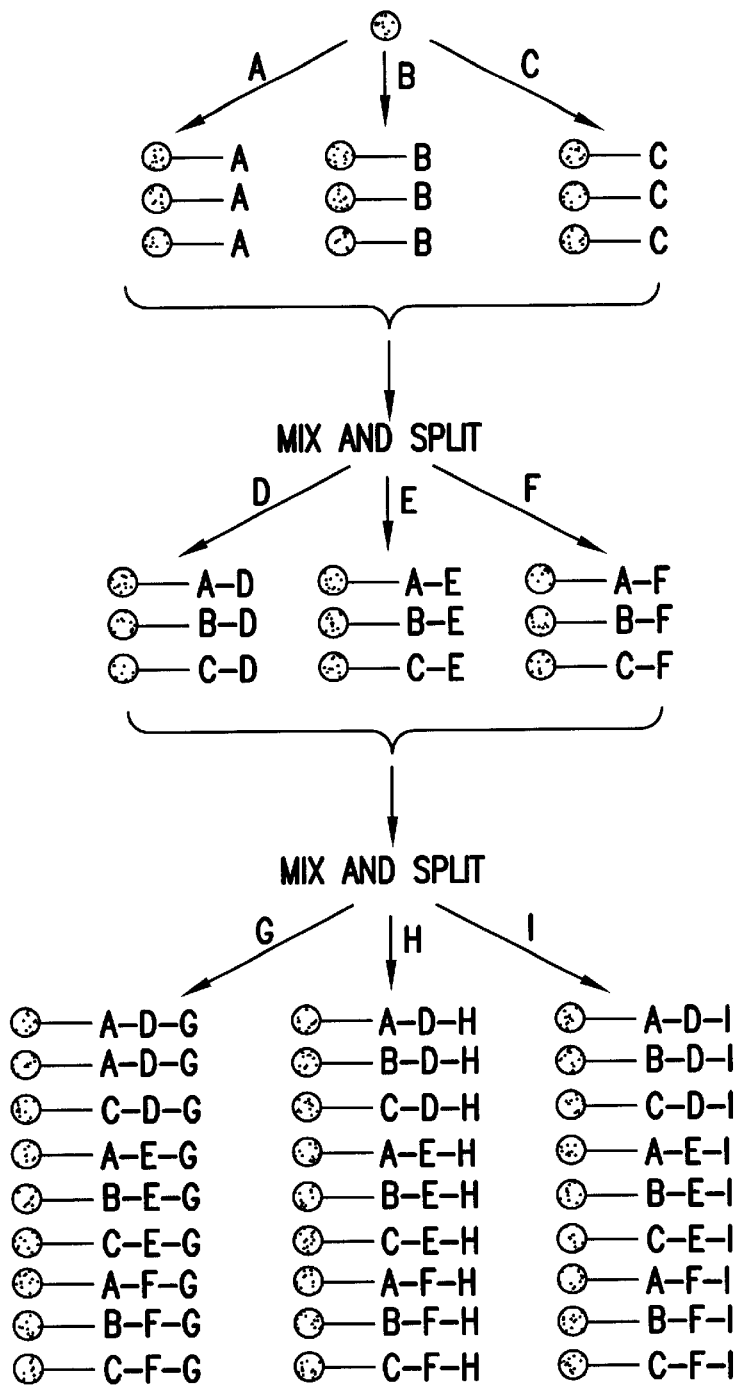
FIG. 1 shows a schematic illustration of the mix and split synthetic method for constructing a combinatorial chemical library.

As used herein, the term "halide" refers to bromo (Br) chloro (Cl), fluoro (F) or iodo (I).

The term resin as used herein refers to resins of the type commonly used in the art of synthetic peptide preparation or in solid phase organic synthesis. Examples of such resins include, but are not limited to methyl benzhydrylamine (MBHA) or benzhydrylamine (BHA) or Merrifield resin (i.e. chloromethylated polystyrene), Wang resin, Tentagel, Rink etc.

Suitable protecting groups for amines include t-butyloxycarbonyl (BOC), benzyloxycarbonyl (Cbz), 9-fluorenylmethyloxycarbonyl (Fmoc), allyloxycarbonyl (Alloc), biphenyloxycarbonyl (Bpoc), and triphenylmethyl (trityl).

Common solvents include N,N-dimethylformamide (DMF), 1,2-dimethoxyethane (DME), Dichloromethane (DCM), Dimethylacetamide (DMA), Common coupling agents for the preparation of amide bonds include: N,N'-dicyclohexylcarbodiimide (DCC), N,N'-diisopropylcarbodiimide (DIC), benzotriazol-1-yloxy-tris(dimethylamino)phosphonium-hexafluorophosphate (BOP), bis(2-oxo-3-oxazolidinyl)phosphine chloride (BOPCl), Bromo-tris-pyrrolidino-phosphonium hexafluoro-phosphate (PyBroP).

Other common abbreviations include: 4-dimethylaminopyridine (DMAP), trifluoroacetic acid (TFA), triethylamine (TEA), 1,3-diaminopropionic acid (DAP).

Within the context of this application, IR and Raman spectroscopy are used interchangeably because they both measure the energy difference between the ground state and excited states of particular functional groups, otherwise known as chromophores. The ordinary artisan would understand that the two are different methods. IR requires a change in dipole moment of such excitation, while Raman requires a change in functional group polarization of such excitation. Thus, a nitrile is suited for both spectroscopies, since it is polarizable and has a dipole. However, an acetylene is more suited for Raman because it is polarizable, and has negligible dipole. However, an acetylene can have significant dipole if each alkyne carbon is attached to significantly different substituents.

All citations herein are incorporated by reference.

B. Coding Process

In combinatorial syntheses, classes of structurally related compounds, or libraries, are constructed on solid supports. Each individual member of the library (e.g., each unique chemical structure) is present in multiple copies on each of a plurality of solid supports. The present invention provides a process of coding individual members of a combinatorial chemical library synthesized on a plurality of solid supports, which process includes the step of covalently attaching to each of the plurality of solid supports a coding identifier detectable by infrared or Raman spectroscopy. The coding identifier is a set of one or several tags and/or incipient tags, detectable by IR and/or Raman spectroscopy. The presence or absence of the identifier on the solid support, or the ratio of one or more identifiers on the solid support provides a code for the unique chemical structure on the support or the chemical steps used to generate that structure.

A library is defined as a collection of unique chemical entities. A library can be prepared using two strategies. In one strategy the library is prepared by the solid phase organic synthesis of discrete compounds on individual solid supports such as beads. The large number of compounds generated in a library is obtained by a mix and split strategy common to combinatorial chemistry. The chemistry to prepare the library can consist of attachment of a suitably protected core with several sites of diversity. At each step of the mix and split strategy, a protecting group is removed and diversomers (diverse reactants that have functionality for chemical attachment) are added. In accordance with a second strategy, the library is made by the sequential addition of each diversiomer to the expanding chemical core derived from previous diversiomers such as solid phase peptide or oligonucleotide synthesis.

In a preferred embodiment, a process of the present invention is used in conjunction with the mix and split method (See FIG. 1). As shown in FIG. 1, a pool of solid supports derivatized with appropriate sites for library synthesis is split into as many subpools as necessary and each subpool is reacted with a different reagent. The subpools are then mixed together and split again, thus insuring a statistical distribution of each derivatized bead in each subpool. The second step of the synthesis is then carried out, and each subpool is reacted with a different reagent. The pools are mixed and split, and another synthetic step is performed. In the example shown in FIG. 1, three reagents are used at each of the three steps, and a total of $3^3=27$ compounds are prepared by carrying out only 3×3=9 reactions, plus two mix and split steps.

In a more general case, if n reagents are used at each step, and m steps are carried out, nm compounds are synthesized by carrying out n×m reactions. Each solid support is derivatized with only one compound. The amount of compound on one solid support depends on the size of the solid support and is in the order of 10 picomoles to 1 nanomole. Compound identification after release from the support using standard analysis methods ($^1$H NMR, $^{13}$C NMR) is therefore impossible unless unusually large beads are used. Mass spectroscopy is commonly used but is rarely sufficient.

Figure 2:
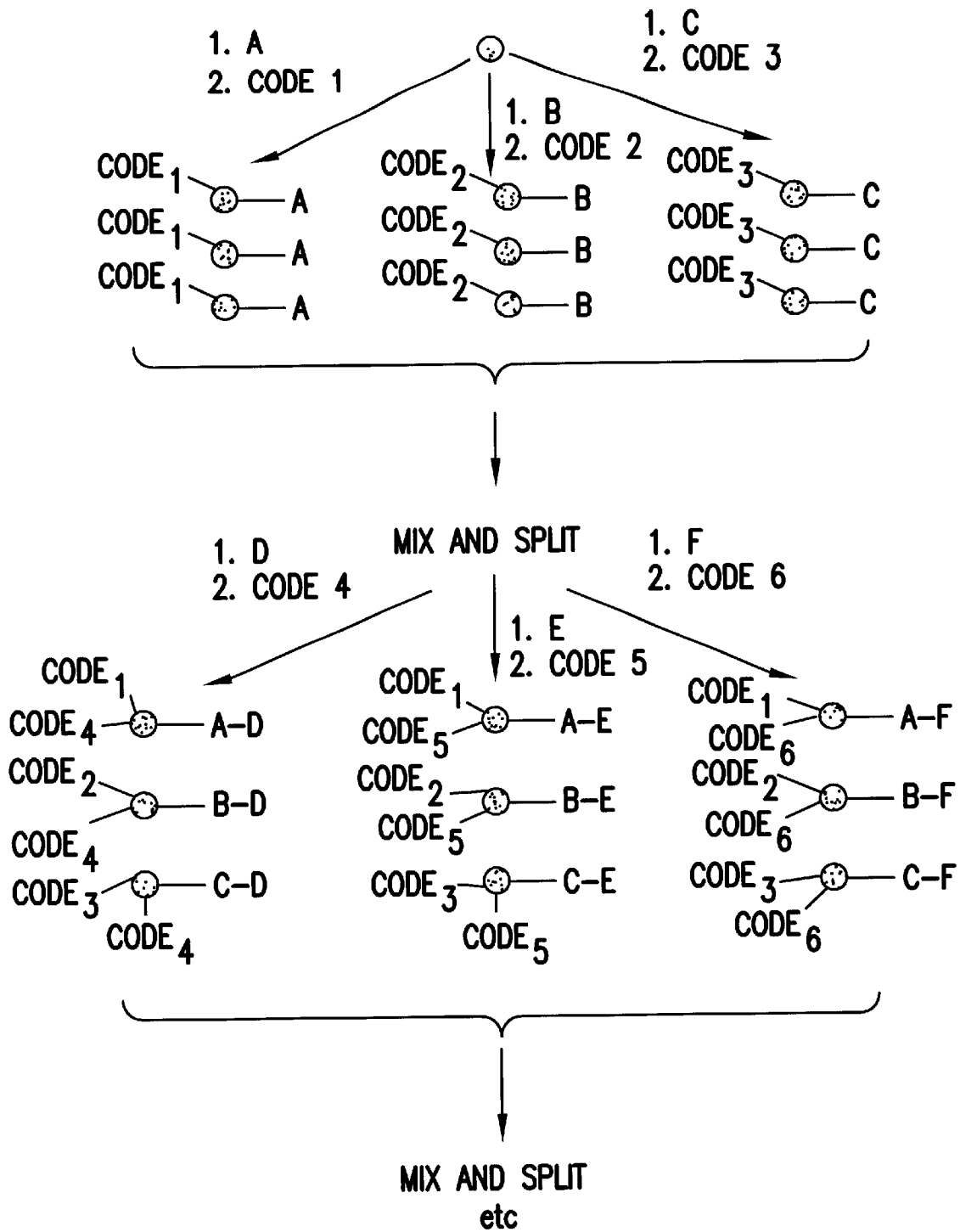
FIG. 2 shows a schematic illustration of the use of coding identifiers (tags) to identify individual members of a combinatorial chemical library made by a mix and split synthetic method.

The use of a coding process of the present invention in conjunction with a mix and split strategy is shown schematically in FIG. 2. At each library chemical step and for each subpool of the library, a set of one or several coding identifiers that are unique to the synthetic step and the reactants used in that step, are covalently attached to the solid support Reading the tags after library synthesis on a particular solid support provides the chemical history of that specific support, and therefore the structure of the particular compound present on that solid support.

In one embodiment, the solid support (e.g., bead) is configured such that there are two sites of incorporation. A first site allows for incorporation of the particular library member via a suitable linker. A second site allows for incorporation of the tag. By way of example, an IR distinctive tag is chemically bound to the epsilon nitrogen of an alpha-protected lysine (Lys), ornithine (Orn) or Dap. Each chemical step is coded by the covalent attachment of an alpha protected Lys, Orn or Dap containing the IR tag(s) to the bead. As each step of the library synthesis proceeds, the alpha protecting group of the Lys, Orn or Dap is removed and then another alpha protected Lys, Orn or Dap with another distinctive IR tag is attached. In this manner, multiple reactions can be tagged.

The alpha protecting group can be a Fmoc, Bpoc, alloc, or another common protecting group whose cleavage is compatible with and orthogonal to the linker and library used. The IR signature of the bead can be read either before or after cleavage and, based on the IR signals observed, the reaction history of the bead can be ascertained.

1. Solid Supports

Solid supports for use in combinatorial chemical syntheses are well known in the art (See, e.g., International Patent Publication No. WO94/08051). A common solid support is a polystyrene bead. Depending upon the nature of the synthetic procedure or the assay of the final product, a particular bead can be more or less desirable. While beads are especially convenient, other solid supports can also find use, such as glass capillaries, hollow fibers such as cotton, etc., where the size of the solid support allows for the desired variation in reaction histories. Any convenient composition can be used for the particles or beads, which bead composition will maintain its mechanical integrity during the various process stages, can be functionalized, has functional groups or allows for reaction with an active species, allows for serial synthesis as well as attachment of the identifiers, can be readily mixed and separated, and will allow for convenient detachment of the tags and products.

One preferred solid support is a bead. Exemplary beads that can be employed include cellulose beads, pore-glass beads, silica gel, polystyrene beads, particularly polystyrene beads cross-linked with divinylbenzene, grafted copolymer beads such as polyethyleneglycol/polystyrene, polyacrylamide beads, latex beads, dimethylacrylamide beads, particularly cross-linked with N,N'-bis-acryloyl ethylene diamine and comprising N-t-butoxycarbonyl-β-alanyl-N'-acryloyl hexamethylene diamine composites, such as glass particles coated with a hydrophobic polymer such as cross-linked polystyrene or a fluorinated ethylene polymer to which is grafter linear polystyrene; and the like. General reviews of useful solid supports (particles) that include a covalently-linked reactive functionality can be found in Atherton et al., Prospectives in Peptide Chemistry, Karger, 101–117 (1981); Amarnath et al., *Chem. Rev.*, 77:183–217 (1977); and Fridkin, The Peptides, Vol. 2, Chapter 3, Academic Press, Inc., (1979), pp. 333–363.

Another preferred solid support is a polystyrene or polyethylene glycol resin. Such resins can be obtained from commercial sources (Wang, NovaSyn-PEG) or prepared in accordance with standard procedures well known in the art. The preparation of a Wang polystyrene resin is described in detail hereinafter in the Examples.

Depending upon the nature of the syntheses, the beads or resin can be functionalized in a variety of ways to allow for attachment of the initial reactant. Functionalities present on the bead can include hydroxy, carboxy, aminohalide, amino, thio, active halogen (Cl or Br) or pseudohalogen (e.g. —CN, toluenesulfonyl, methanesulfonyl, bromosulfonyl, triflurosulfonyl or the like). In selecting the functionality, some consideration should be given to the fact that the identifiers will usually also become bound to the bead. Consideration will include whether the same or a different functionality should be associated with the product and the identifier, as well as whether the two functionalities will be compatible with the product or identifier attachment and tag detachment stages, as appropriate. Different linking groups can be employed for the product, so that a specific quantity of the product can be selectively released. In some instances the support can have protected functionalities which can be partially or wholly deprotected prior to each stage, and in the latter case reprotected. For example, an amino group can be protected with a carbobenzoxy group as in polypeptide synthesis, a hydroxy group with a benzyl ether, etc.

2. Coding Identifiers

Coding identifiers used in accordance with a process of the present invention can be any chemical compound capable of covalent attachment to the solid support and which chemical compound can be readily detected. In a preferred embodiment, the identifiers are infrared (IR) or Raman active chromophores. Such chromophores are well known in the art. To distinguish the identifier from chemical structures in the combinatorial library, it is preferred that the coding identifiers have absorption bands in the region of from about 1700 cm$^{-1}$ to about 2500 cm$^{-1}$. Exemplary and preferred chromophores with absorption bands in the 1700 to 2500 cm$^{-1}$ range are nitrites, acetylenes, cyclopentylketones, gamma-lactones, deuterated organics and the like. Table 1, below, shows the structure and characteristic absorption wavenumbers of exemplary nitrile and acetylene tags for IR and Raman spectroscopy, respectively. However, Table 1 is not intended to be limiting.

TABLE 1a

| Nitile Containing Compound | Nitrile Wavenumber (cm$^{-1}$) |
|---|---|
| 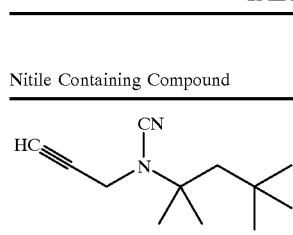 | 2204 |
| 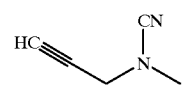 | 2217 |
| 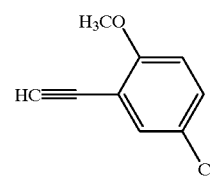 | 2226 |
| 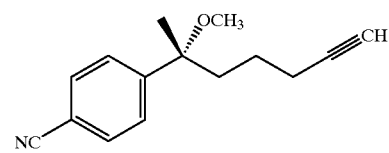 | 2229 |
| 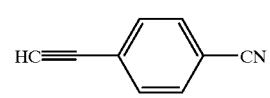 | 2231 |
|  | 2247 |

TABLE 1a-continued

| Nitile Containing Compound | Nitrile Wavenumber (cm$^{-1}$) |
|---|---|
| 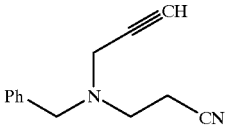 | 2249 |
| 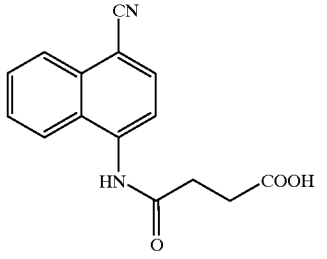 | 2220 |
| 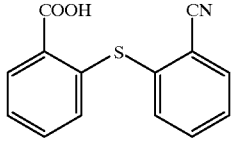 | 2223 |
| 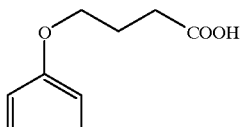 | 2224 |
| 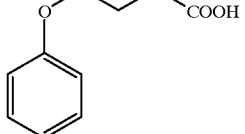 | 2226 |
| 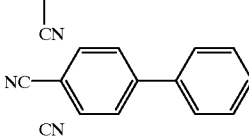 | 2228 |
| 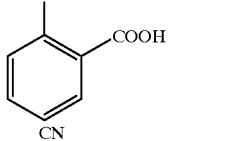 | 2230 |
| 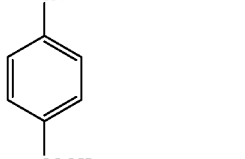 | 2232 |
| 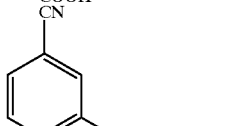 | 2242 |
| 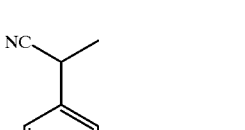 | 2246 |

TABLE 1a-continued

| Nitrile Containing Compound | Nitrile Wavenumber (cm$^{-1}$) |
|---|---|
| NC—CH$_2$CH$_2$—COOH | 2250 |
| NC—CH$_2$—C$_6$H$_4$—O—(CH$_2$)$_3$—COOH | 2253 |

TABLE 1b

| Acetylene Containing Compound | When Attached to Lysine via Amide Acetylene Wavenumber (cm$^{-1}$) |
|---|---|
| HC≡C—CH$_2$CH$_2$—C≡C—CH$_2$CH$_2$CH$_3$ | 2226 cm$^{-1}$ (attached directly to polystyrene, not lysine) |
| Tag 1: H$_3$CO—C$_6$H$_4$—C≡C—C$_6$H$_4$—COOH | 2216 cm$^{-1}$ |
| Tag 2: C$_6$H$_5$—C≡C—C$_6$H$_4$—COOH | 2217 cm$^{-1}$ |
| Tag 3: F—C$_6$H$_4$—C≡C—C$_6$H$_4$—COOH | 2218 cm$^{-1}$ |
| C$_6$H$_5$—C≡C—COOH | 2220 cm$^{-1}$ |

TABLE 1b-continued

| Acetylene Containing Compound | When Attached to Lysine via Amide Acetylene Wavenumber (cm$^{-1}$) |
|---|---|
| Tag 4: thiazol-2-yl—C≡C—(CH$_2$)$_7$—COOH | 2231 cm$^{-1}$ |
| Tag 5: pyrimidin-2-yl—C≡C—(CH$_2$)$_7$—COOH | 2236 cm$^{-1}$ |
| Tag 6: diyne long chain—COOH | 2256 cm$^{-1}$ |
| Tag 7: 2-Ph-C$_6$H$_4$—C≡C—(CH$_2$)$_6$—COOH | 2228 cm$^{-1}$ |
| 2-OCH$_3$-C$_6$H$_4$—C≡C—(CH$_2$)$_6$—COOH | 2231 cm$^{-1}$ |
| 2-F-C$_6$H$_4$—C≡C—(CH$_2$)$_6$—COOH | 2233 cm$^{-1}$ |

Where the chemical reactions used to construct the combinatorial library are such that they may interfere with attachment of a coding identifier, the actual infrared or Raman active chromophore may be formed later from an incipient IR or Raman tag attached to the solid support.

Exemplary incipient tags are compounds containing a protected amine, protected thiol, aldehyde, oxime, primary amide or N-formyl group. Specific examples of incipient (R) tags and their resultant active chromophores ($R_1$ and $R_2$) are shown below in Table 2.

TABLE 2

| | R<br>Incipient tag attached via amide linkage to bead | $R_1$<br>Incipient tag after removal of protecting group | $R_2$<br>Incipient tag after activation |
|---|---|---|---|
| 1 | 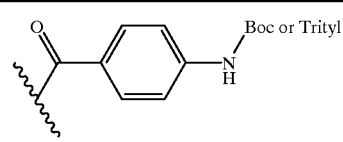 | 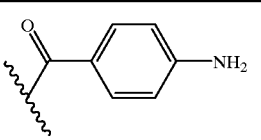 | 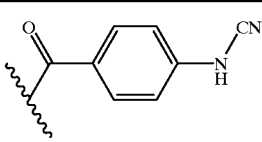 |
| 2 | 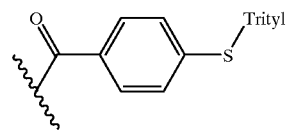 | 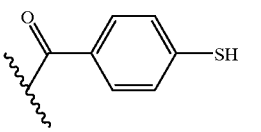 | 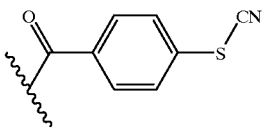 |
| 3 | 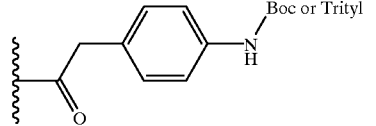 | 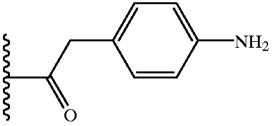 | 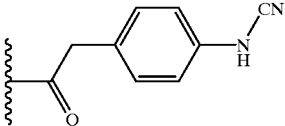 |
| 4 | 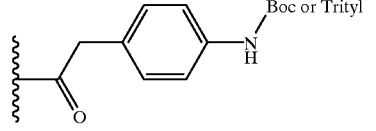 | 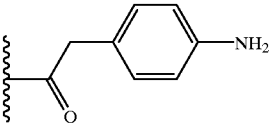 | 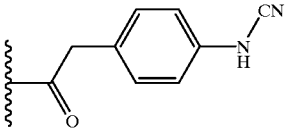 |
| 5 | 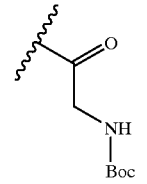 | 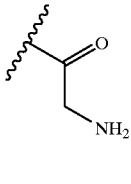 | 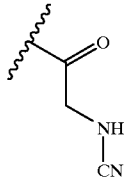 |
| 6 | 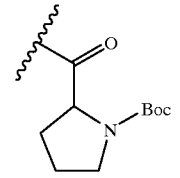 | 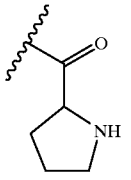 | 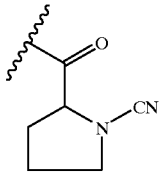 |
| 7 | 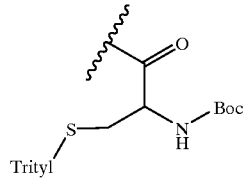 | 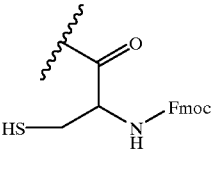 | 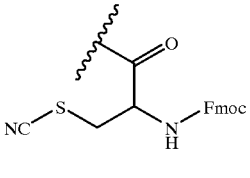 |
| 8 | 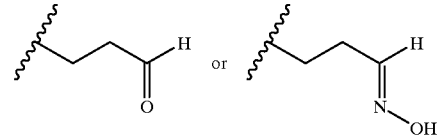 | 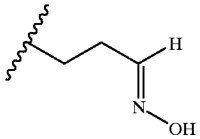 | 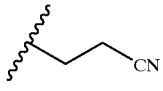 |

TABLE 2-continued

| R<br>Incipient tag attached via amide linkage to bead | R₁<br>Incipient tag after removal of protecting group | R₂<br>Incipient tag after activation |
|---|---|---|
| 9 ~CH₂-NH-CHO | ~CH₂-NH-CHO | ~CH₂-N≡C |
| 10 ~CH₂-C(O)-NH₂ | ~CH₂-C(O)-NH₂ | ~CH₂CH₂-CN |

Figure 5:
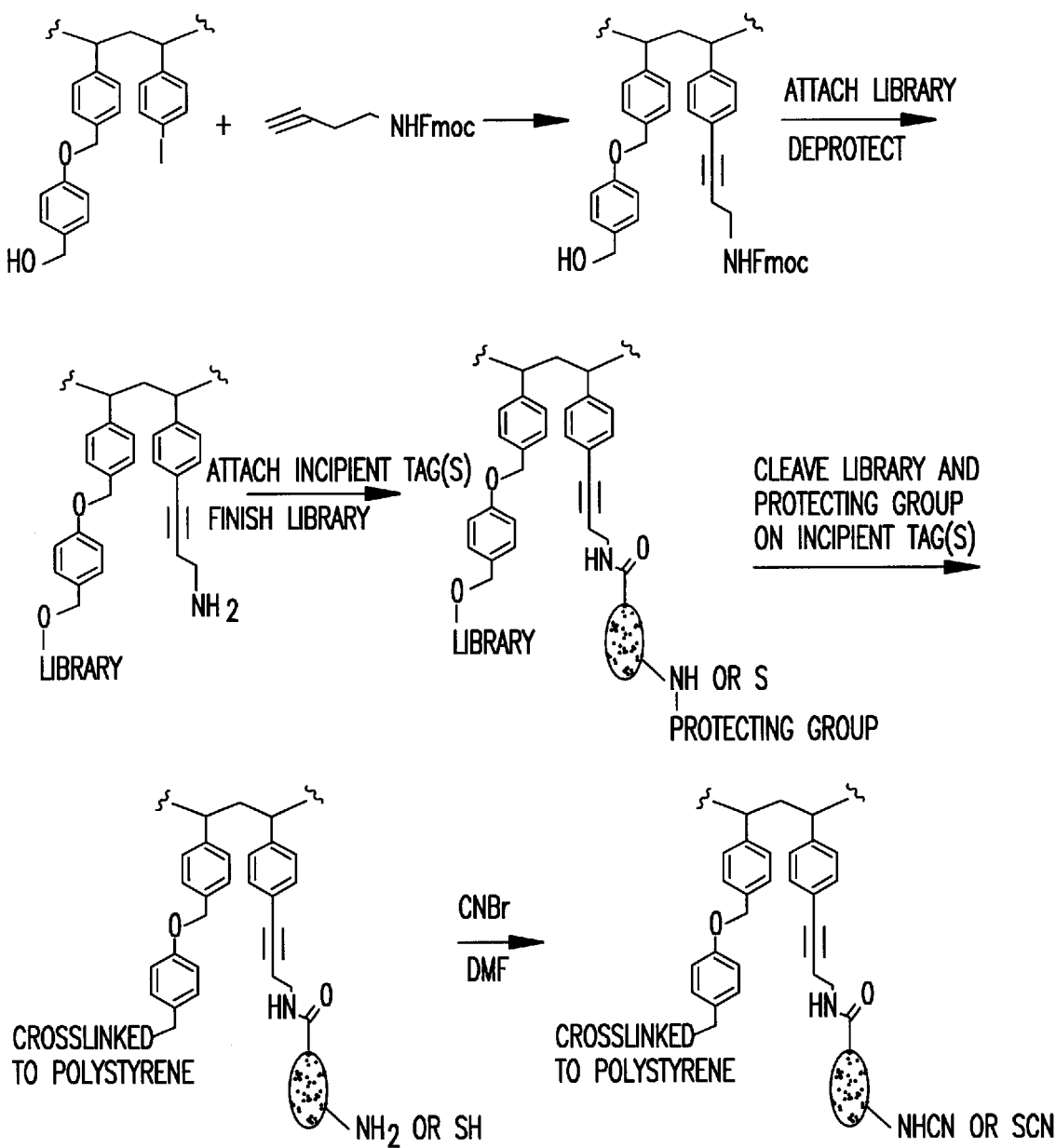
FIG. 5 shows a schematic illustration of the use of incipient tags to code members of a combinatorial chemical library.

A schematic illustration of the use of such incipient identifier is shown in FIG. 5. As shown in FIG. 5, an incipient IR tag can be covalently attached to a free amine of polystyrene resin via an amide bond coupling reaction. Following release of the novel chemical entity from the bead and deprotecting any functional groups on the incipient tag, the IR tag is activated and read by chemically derivatizing the incipient tag.

Methods of activation include using cyanogen bromide or phosphorous oxychloride to form cyanamides, thiocyanates, nitrites and isonitriles. Specific examples of activation means are set forth below.

Cyanamides from Amines

The bead derivitized with a free amine is immersed in a 0.25M solution of cyanogen bromide in DMF. After 18 hours the bead is removed and washed with DMF, DCM, and diethyl ether.

Thiocyanates from Thiols

The bead derivitized with a free thiol is immersed in a 0.25M solution of cyanogen bromide in DMF. After 18 hours the bead is removed and washed with DMF, DCM, and diethyl ether.

Nitriles from Aldehydes
(First Form Oxime then Dehydrate Oxime)

Oxime formation: The bead is immersed in a solution of 0.25M solution of 1:1 hydroxylamine hydrochloride-TEA in 1:1 THF-ethanol. After 18 hours the bead is removed and washed with methylene chloride and methanol.

Nitrile from oxime: The bead is immersed in a solution of 0.25M solution of POCl₃ in 1,2-dichloroethane. The solution is heated to reflux for 2 hours. The solution is cooled and the bead is removed and washed with DCM and methanol.

Alternatively the bead is immersed in neat POCl₃ and heated to reflux for 2 hours. The solution is cooled the bead is removed and washed with DCM and methanol.

Nitriles from Primary Amides

The bead is immersed in a solution of 0.25M solution of POCl₃ in 1,2-dichloroethane. The solution is heated to reflux for 2 hours. The solution is cooled and the bead is removed and washed with DCM and methanol.

Alternatively the bead is immersed in neat POCl₃ and heated to reflux for 2 hours. The solution is cooled the bead is removed and washed with DCM and methanol.

Isonitriles from N-formylamides

The bead is immersed in a solution of 0.25 M POCl₃ in 1,2-dichloroethane. The solution is heated to reflux for 2 hours. The solution is cooled and the bead is removed and washed with DCM and methanol. Alternatively the bead is immersed in neat POCl₃ and heated to reflux for 2 hours. The solution is cooled the bead is removed and washed with DCM and methanol.

Multiple Codes

Figure 6:
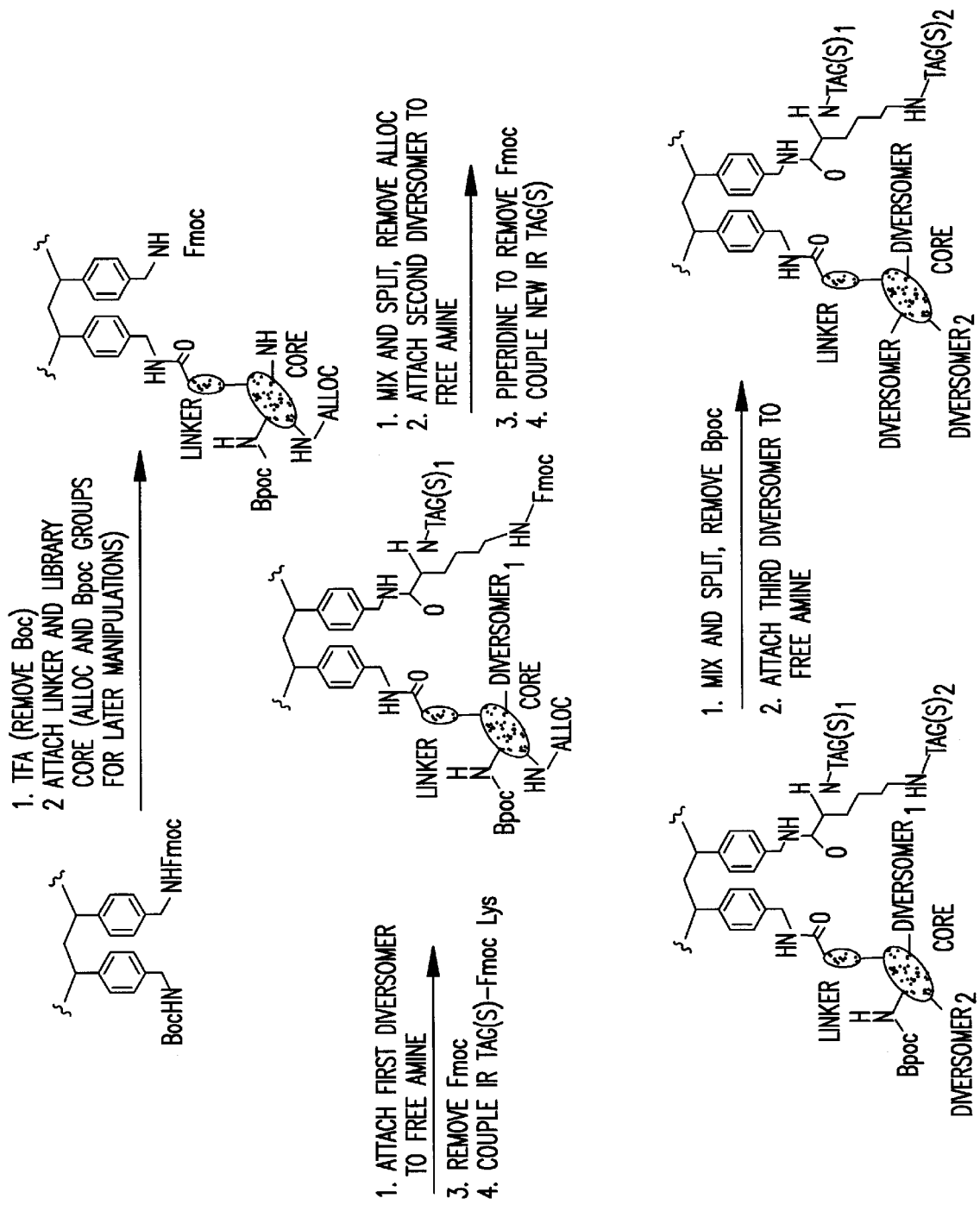
FIG. 6 shows a schematic illustration of the use of linkers and tags or incipient tags to code members of a combinatorial chemical library.

A process using incipient tags can be repeated for the coding of as many chemical steps as is required (See FIG. 6). In accordance with FIG. 6, Boc and Fmoc protected amine groups are subjected to treatment with TFA to remove the Boc protecting group. A desired linker and library scaffold is then attached to the deprotected amine. The scaffold group contains Alloc and Bpoc protecting groups for later manipulation. The Alloc protecting group can be removed, for example, by treatment with palladium (Pd(O)). A first set of diversomers can then be attached to the core. The Fmoc protecting group on the other amine is then removed, by example, with treatment with piperidine.

Following deprotection of the amine, an incipient tag is attached to the free amine. Following a mix and split step, the Bpoc protecting group is removed and a second set of diversomers is added to the library member. A second treatment with piperidine removes the Fmoc protecting group on the incipient tag and allows for the coupling of new tags. The mix and split methods with deprotection in addition of subsequent monomers can then be continued until a single bead is derivatized with both tags and the desired library member. The advantage of this system is that the release of the library member from the bead does not promote release of the tags. Analysis after cleavage, via the necessary spectrophotometric method, allows for single-bead compound identification.

Although described for incipient tags, multiple codes can also be used for intact tags.

3. Attachment of Coding Identifier to Solid Support.

The identifiers are covalently attached to the solid support. The precise means for covalently attaching the identifiers to the solid support will depend, as is well known in the art, on the chemical structure of the identifier and the nature of the solid support. By way of example, covalent attachment of a nitrile-acid identifier to a polystyrene solid support can be accomplished by amide bond formation of the nitrile-acid to an amine functionality on the polystyrene bead. Where the coding identifier is an acetylene-nitrile, covalent attachment to the solid support can be accomplished using palladium catalyzed acetylene coupling to a halo-aromatic group generated on the solid support. A detailed description of such linking strategies can be found hereinafter in the Examples.

Figure 3:
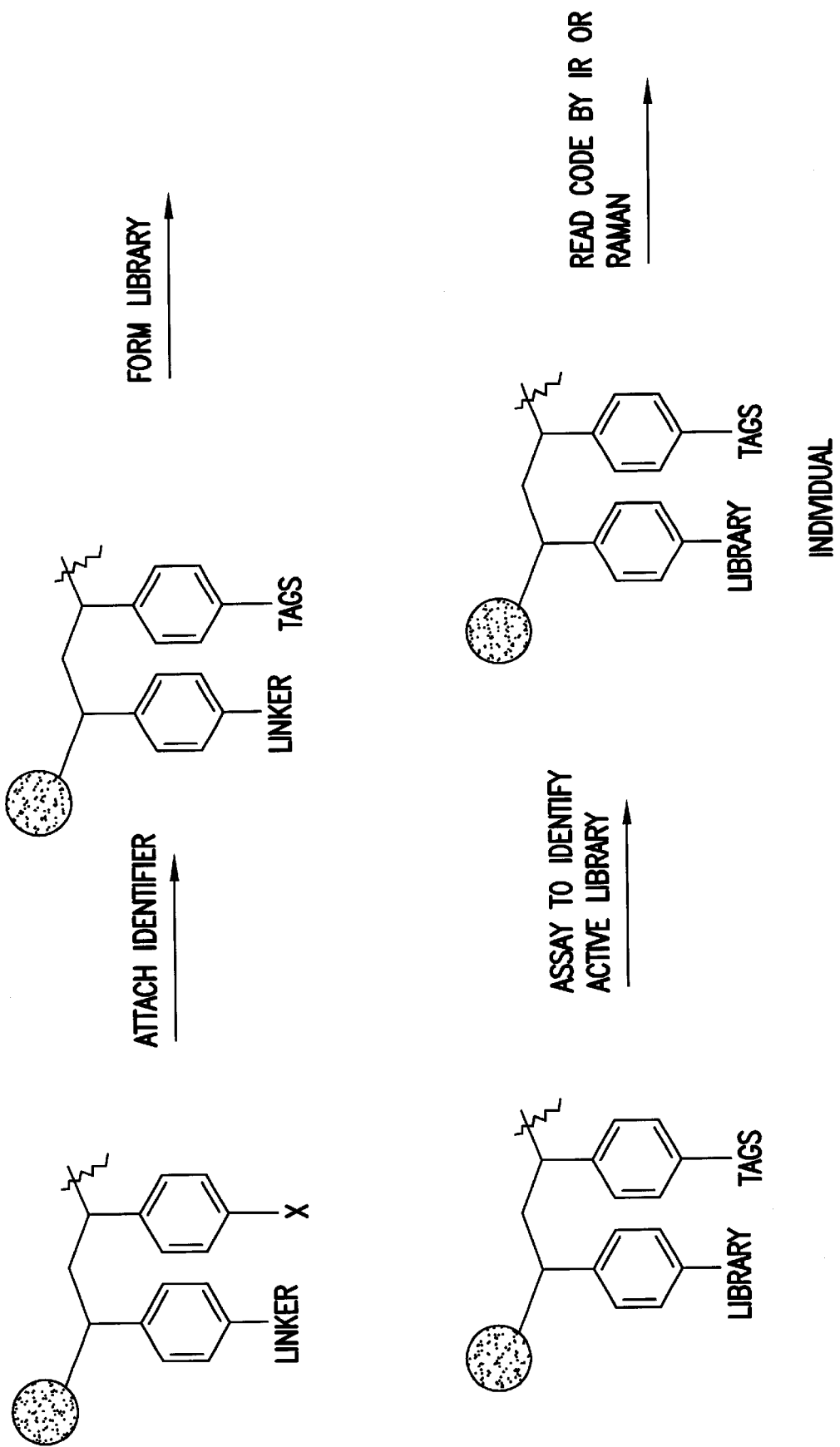
FIG. 3 shows a schematic illustration of a first embodiment of the use of linkers and tags in the formation of a combinatorial chemical library.
Figure 4:
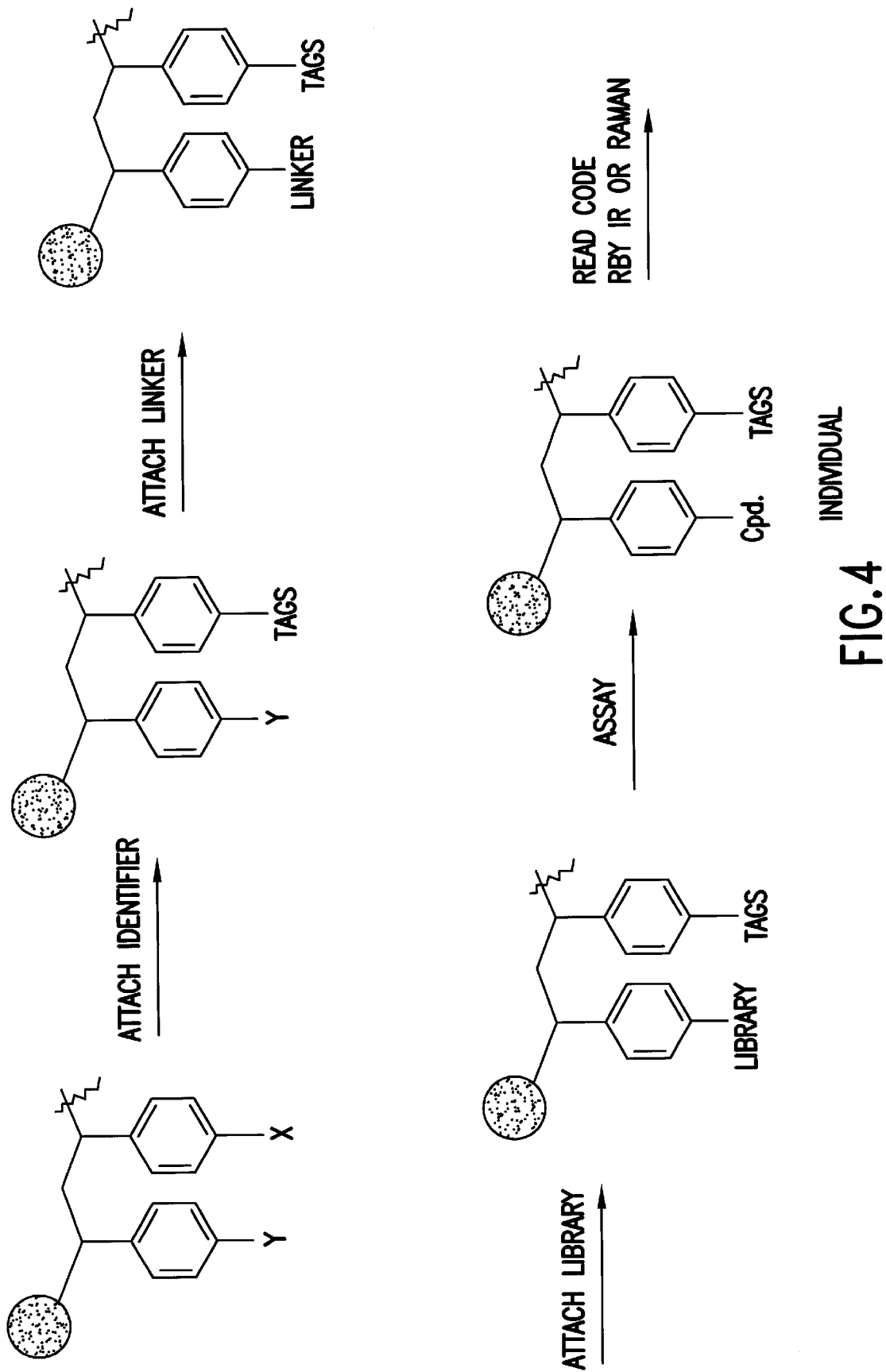
FIG. 4 shows a schematic illustration of a second embodiment of the use of linkers and tags in the formation of a combinatorial chemical library.

Use of the methods disclosed above results in a direct covalent linkage of the identifier to the solid support. In an alternate embodiment, a linking moiety or linker is disposed between the support and the identifier. Where a linker is employed, attachment to the solid support can occur either before (See FIG. 3) or after (FIG. 4) attachment of the coding identifier or tag.

Where detachment of the product is desired, there are numerous functionalities and reactants which can be used. Conveniently, ethers can be used, where substituted benzyl ether or derivatives thereof, e.g., benzylhydryl ether, indanyl ether, etc. can be cleaved by acidic or mild reductive conditions. Alternatively, one can employ β-elimination, where a mild base can serve to release the product. Acetals, including the thio analogs thereof, can be employed, where mild acid, particularly in the presence of a capturing carbonyl compound, can serve. By combining formaldehyde, HCl and an alcohol moiety, an α-chloroether is formed. This can then be coupled with a hydroxy functionality on the bead to form the acetal. Various photolabile linkages can be employed, such as O-nitrobenzoyl, 7-nitroindanyl, 2-nitrobenzhydryl ethers or esters, etc. Esters and amides can serve as linkers, where half-acid esters or amides are formed, particularly with cyclic anhydrides, followed by reaction with hydroxyl or amino functionalities on the bead, using a coupling agent such as DCC. Peptides can be used as linkers, where the sequence is subject to enzymatic hydrolysis, particularly where the enzyme recognizes a specific sequence. Carbonates and carbamates can be prepared using carbonic acid derivatives, e.g., phosgene, carbonyl diimidazole, etc. and mild base. The linker can be cleaved using acid, base or a strong reductant.

Where a linker is used, functionalities on the solid support can be modified through a non-labile linkage such as an ester bond, amide bond, amine bond, ether bond, or through a sulfur, silicon, or carbon atom, depending upon whether one wishes to be able to remove the product from the bead or resin. Conveniently, the bond to the bead or resin is permanent. Alternately, the bond between the linker and bead or resin can be labile or cleavable. Depending upon the nature of the linking group bound to the particle, reactive functionalities on the bead may not be necessary where the manner of linking allows for insertion into single or double bonds, such as is available with carbenes and nitrenes or other highly-reactive species. In this case, the cleavable linkage can be provided in the linking group which joins the product to the bead.

A preferred linker is a Lys, Orn, or Dap linker protected with a photocleavable protecting group at the epsilon, gamma or delta amino group. Limited irradiation produces partial cleavage of this photocleavable group, therefore liberating a site for the incorporation of the IR or Raman tags. A schematic illustration of the use of such a linker is shown in FIG. 7.

Figure 7:
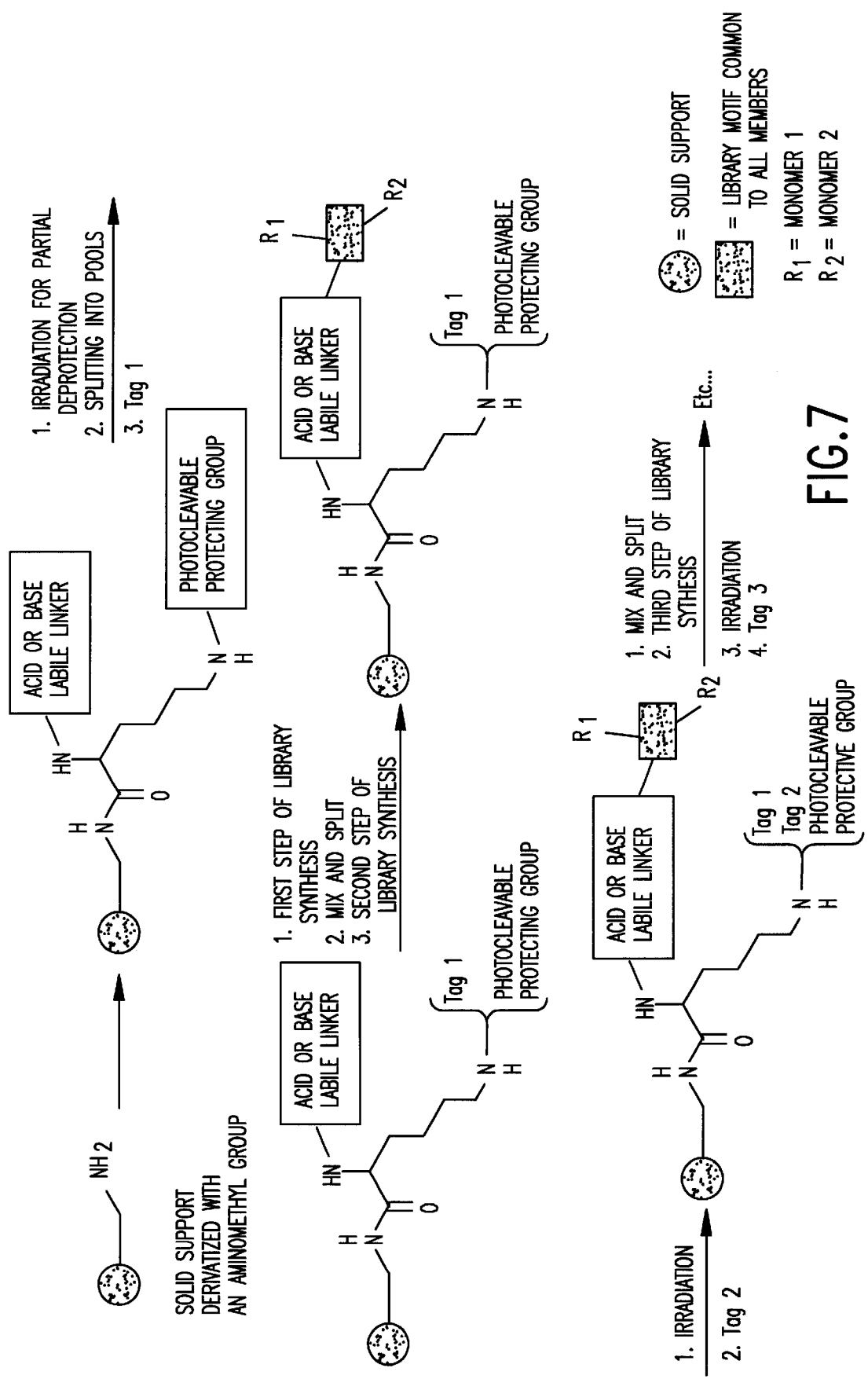
FIG. 7 shows the use of a lysine linker to attach coding identifiers (tags) to solid supports in a combinatorial chemical library.

As shown in FIG. 7, a commercially available polystyrene (PS) or polystyrene/polyethylene glycol (PS/PEG) resin derivatized with an aminomethyl group is coupled to an orthogonally functionalized lysine, or ornithine or Dap-based unit. The alpha amino group is derivatized with an acid or base labile linker on which to construct the library. An example of such a linker is a protected 4-hydroxymethyl phenoxyacetic acid (Wang linker) bearing a protective group masking the alcohol functionality. The delta, gamma or epsilon amino acid is derivatized with a photocleavable protecting group.

A first coding identifier (Tag 1) is incorporated by submitting the resin to light for a limited time to effect partial protecting groups cleavage at the epsilon position, thus partially liberating the reactive amino functionality. This amine is then coupled with an IR or Raman coding identifier using standard chemical reactions (e.g., amide formation if the IR or Raman tag contains a carboxylic acid moiety). Pools of differently coded resin are then obtained. The first step of the library synthesis is conducted, followed by a mix and split step. The second step of the library synthesis is carried out, followed by irradiation to partly remove the remaining protecting group on the epsilon-amino group.

A second coding identifier (Tag 2) is then introduced and the pools are again mixed and split. This process can be repeated for the coding of as many chemical steps as is required. At the end of the synthesis, a single bead is derivatized with the coding identifier and the library member. Release of the library member from the bead does not promote release of the coding identifier. Analysis of the after-cleavage bead via the necessary spectroscopic method allows for single-bead compound identification.

II Identifying Process

In a related aspect, the present invention provides a process of identifying individual members of a combinatorial chemical library. The differential attachment of one or more tagging identifiers at each step during the synthesis at which it is deemed desirable to code to individual pools of the solid support material generates a code. Upon completion of synthesis of a combinatorial library containing the above mentioned coding identifiers, the individual synthetic path from which any bead was generated can be identified by acquiring an Infrared or Raman spectrum of this bead, either before or after the library chemical entity has been removed. An analysis of the band frequencies observed by either (or both) spectroscopic technique(s) leads to an unique assignment of the synthetic pathway.

IR or Raman active tags can be employed to generate a code by virtue of either their presence or absence (i.e., in a binary code manner such as 001, 010, 100, 011, 101, 111), or by a multi-code signature in which ratio of tags to one another is also significant (i.e., tag-1/tag-2 (1:1), tag-1/tag-2 (4:1), tag-1/tag-2 (1:4), etc.), or where the ratio of to some external standard such as a polystyrene band is also significant (i.e., tag-1/tag-2 (1:1), tag-1/tag-2 (2:2), etc.).

By providing N coding identifiers, each having M distinguishable states, $M^N$ different syntheses can be uniquely coded. Where M=2 (e.g., the two states could be the presence or absence of the identifier), the synthesis would be defined by a base 2 or binary code. In the case of M=3 (where the three states could be the presence of an identifier at two distinguishable concentrations or its absence), the synthesis would be defined by a base 3 code. Where M>2, codes are termed higher order codes. The advantage of higher order codes over a binary code is that fewer identifiers are required to encode the same quantity of information about the synthesis. The products which are produced will be defined as resulting from a serial synthesis. At each stage in the synthesis, there is available a plurality of reactants and/or reagents and/or conditions, which result in a feature of the product in relation to an identifiable and usually separable entity, e.g. tag. The synthesis can involve individual reactants which become incorporated into the product. Alternatively, a stage can involve one or more reactions which results in a modification of a reaction intermediate. In many cases, combinations of these possibilities will be involved.

Using a base 2 or binary code (M=2) and three identifiers (N=3), as many as 8 ($2^3$) agents for a given stage in a synthesis can be encoded. Similarly, even more information about the synthesis can be encoded by more identifiers. For example, 9 identifiers (N=3) and a base 2 code (M=2) would allow up to $2^9$ or 512 different reagent choices to be encoded. An example of the use of a binary code using six identifiers is illustrated below. The six identifiers are designated as $R_1$–$R_6$.

$R_1$ 2195 cm$^{-1}$
$R_2$ 2218 cm$^{-1}$
$R_3$ 2207 cm$^{-1}$
$R_4$ 2244 cm$^{-1}$
$R_5$ 2225 cm$^{-1}$
$R_6$ 2250 cm$^{-1}$

For the purpose of this illustration, identifiers $R_1$ through $R_6$ are used in a mix and split method as described above and illustrated in FIGS. 1 and 2. The individual members of the combinatorial library are identified by spectrophotometric analysis of each pool. A binary code is used to determine the presence (Y) or absence (N) of each identifier. Exemplary results of such an analysis are shown below in Table 3.

TABLE 3a

| Pool | R1 | R2 | R3 | Code |
|------|----|----|----|------|
| A | Y | N | N | (100) |
| B | N | Y | N | (010) |
| C | N | N | Y | (001) |
| D | Y | Y | N | (110) |
| E | Y | N | Y | (101) |
| F | N | Y | Y | (011) |
| G | Y | Y | Y | (111) |
| H | N | N | N | (000) |

TABLE 3b

| Pool | R4 | R5 | R6 | Code |
|------|----|----|----|------|
| X | Y | N | N | (100) |
| Y | N | Y | N | (010) |
| Z | N | N | Y | (001) |

The identification of the chemical nature or synthetic steps used to construct an unknown can be accomplished by determining the binary code for that unknown and comparing it to the predetermined binary codes from Table 3. By way of example, where an unknown demonstrates spectrophotometric activity only at wavelengths of 2207 cm$^{-1}$ and 2225 cm$^{-1}$ (that is, a binary code of $R_3$ and $R_5$=001 010) would indicate that the unknown was created using pools C and Y.

Use of a base 3 code (M=3) allows for coding and identification of greater numbers of library members with use of the same or fewer identifiers. By way of example, using a base 3 code (M=3) and three identifiers (N=3) would allow as many as 27 ($3^3$) library members to be encoded and identified.

Yet another means of identifying library members in accordance with a process of present invention involves determining the ratio of coding identifiers on individual solid supports. An example of such a means of identifying is shown below in Table 4. The information in Table 4 illustrates the formation of 25 pools of tagged solid supports using the acetylene-nitrile identifiers shown in Table 1.

TABLE 4

| Code | Tag(s) | Ratio (Molar) |
|------|--------|---------------|
| 1 | 2204 | — |
| 2 | 0000/2204/2226 | — |
| 3 | 2204/2226 | (1:2) |
| 4 | 2204/2226 | (1:4) |
| 5 | 2226 | — |
| 6 | 2217 | — |
| 7 | 2217/2229 | (1:1) |
| 8 | 2217/2229 | (1:2) |
| 9 | 2217/2229 | (1:4) |
| 10 | 2229 | — |
| 11 | 2231 | — |
| 12 | 2231/2247 | (1:1) |
| 13 | 2231/2247 | (4:1) |
| 14 | 2231/2247 | (1:4) |
| 15 | 2247 | — |
| 16 | 2204/2249 | (1:1) |
| 17 | 2204/2249 | (1:2) |
| 18 | 2204/2249 | (1:4) |
| 19 | 2204/2226/2247 | (1:1:1) |
| 20 | 2204/2226/2247 | (1:2:2) |

TABLE 4-continued

| Code | Tag(s) | Ratio (Molar) |
|------|--------|---------------|
| 21 | 2204/2226/2247 | (1:4:2) |
| 22 | 2204/2226/2247 | (1:2:4) |
| 23 | 2217/2229/2249 | (1:4:4) |
| 24 | 2217/2229/2249 | (1:4:8) |
| 25 | 2217/2229/2249 | (1:8:4) |

A detailed description of the use of such a ratio method of identification is described in detail hereinafter in the Examples.

The Examples that follow illustrate preferred embodiments of the present invention and are not limiting of the claims or specification in any way. One of ordinary skill in the art will readily appreciate that changes and modifications to those embodiments can be made without departing from the true scope and spirit of the invention.

EXAMPLES

Example 1
Synthesis of Tagged Wang Resin

Chromium trioxide ($CrO_3$, 7.0 grams, 70 mM) was placed in a flask under argon atmosphere. Trimethylsilyl chloride (($CH_3$)$_3$SiCl, 9.7 mL, 76 mM) was added via syringe over 5 minutes and the solution was stirred at 35° C. for 30 minutes. DCM (200 mL) was added and argon gas bubbled vigorously through the suspension to volatilize excess ($CH_3$)$_3$SiCl. Iodine ($I_2$, 12.2 g, 48 mM) and polystyrene (10 g, 96 mM) were added and the suspension stirred vigorously for 4 hours at ambient temperature. A solution of saturated sodium bisulfite was then slowly added until an orange to green color change was observed in the suspension and bubbling was no longer observed. The suspension was transferred to a fritted glass filter funnel and the resin was washed sequentially with distilled water, DMF, water, 2 N HCl, distilled water, DMF, distilled water, methanol, DCM, and methanol (500 mL aliquots allowing 5 minutes for each solvent to equilibrate). The p-iodopolystyrene shown below) thus formed was dried under vacuum and stored.

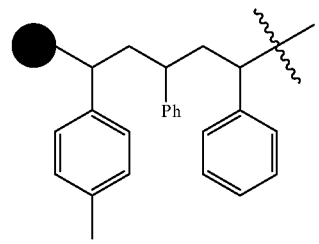

The p-iodopolystyrene synthesized above (5 g) was dissolved in dried DCM (200 mL, distilled from CaH), allowed to swell for 1 hour at room temperature, and then cooled to 0° C. in an ice bath under an argon atmosphere. Chloromethyl methyl ether (10 mL, 130 mM) and $SnCl_4$ (90.5 mL, 4.3 mM) was added slowly to this stirred suspension via separate syringes. The suspension was stirred an additional hour at 0° C. under argon atmosphere, transferred to a fritted filter funnel and washed sequentially with dioxane/distilled water (1:1), dioxane/2 N HCl (1:1), distilled water, dioxane, distilled water, methanol, DCM, and methanol (500 mL aliquots allowing 5 minutes for each solvent to equilibrate). The product, p-iodo-p-chloromethylpolystyrene (shown below), was dried under vacuum and stored. Elemental analysis indicated: Cl=11.61% by weight, I=24.93% by weight.

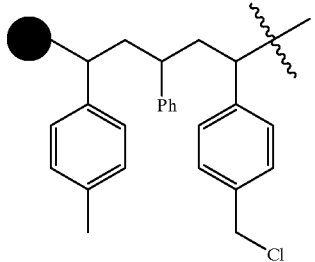

The chloromethyl iodopolystyrene (3.22 grams) was dissolved in DMA (100 mL) and allowed to swell at room temperature for 30 minutes. 4-Hydroxybenzyl alcohol (7.7 g, 62 mM) and sodium methoxide (1.7 g, 31 mM) were added to the suspension and the reaction mixture heated to reflux under an argon atmosphere for 48 hours. The suspension was allowed to cool to room temperature, transferred to a fritted filter funnel and washed sequentially with dioxane/distilled water (1:1), dioxane/2 N HCl (1:1), distilled water, dioxane, distilled water, DMF, distilled water, DMF, distilled water, methanol, DCM, and methanol (500 mL aliquots allowing 5 minutes for each solvent to equilibrate). The product (Wang iodopolystyrene, shown below) was dried under vacuum and stored.

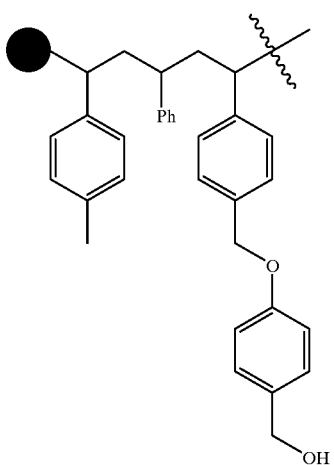

Wang iodopolystyrene (100 mg) synthesized as described above was dissolved in a solvent mixture of DMF/distilled water/TEA (9:1:1) (5 mL total solvent volume) and allowed to swell for 30 minutes at room temperature. A premixed solution of DMF (0.5 mL) containing 5-cyano-1-pentyne (100 mg, 1.07 mM) and 2-methoxy-5-cyano-phenylacetylene (50 mg, 0.32 mM) was added to the polymer bead suspension. Potassium carbonate (50 mg, 0.36 mM) and tetrabutylammonium bromide (50 mg, 0.16 mM) were added and the suspension was stirred under argon atmosphere for 30 minutes. Tetrakis (triphenylphosphine) palladium (O) (25 mg, 0.02 mM) was added rapidly. The reaction mixture was heated to 80° C. and agitated at that temperature under an argon atmosphere for 16 hours and then allowed to cool to room temperature. When the mixture reached room temperature, a saturated solution of ammonium acetate (5 mL) was added and the mixture agitated at room temperature for 30 minutes. Dimethoxyethane (5 mL) was then added and the mixture agitated for an additional 30 minutes, transferred to a fritted filter funnel and washed sequentially with distilled water, DMF, distilled water, 2 N HCl, distilled water, DMF, distilled water, methanol, DCM and methanol (50 mL of each which was allowed to equilibrate for 10 minutes between washes) to yield tagged Wang resin (shown below where $R_1$ is either the 5-cyano-1-pentyne or the 2-methoxy-5-cyano-phenylacetylene derivative, and where both may reside on a single bead).

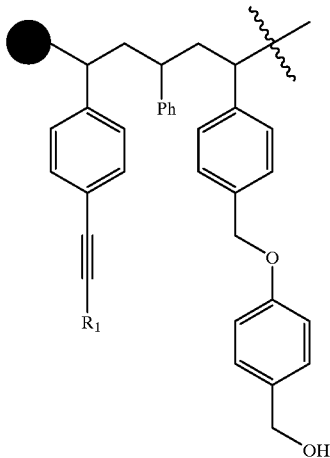

Example 2
Synthesis of & Decoding a Tagged Combinatorial Library
A. Producing Differentially Tagged Wang
1. Tagged Wang #1

Wang iodopolystyrene (100 mg) synthesized as described in Example 1 was dissolved in a solvent mixture of DMF/distilled water/TEA (9:1:1) (5 mL) and allowed to swell for 30 minutes at room temperature. A premixed solution of DMF (0.5 mL) containing 5-cyano-1-pentyne (50 mg, 0.53 mM) and 2-methoxy-5-cyano-phenylacetylene (50 mg, 0.32 mM) was added to the polymer bead suspension followed by potassium carbonate (50 mg, 0.36 mm), tetrabutylammonium bromide (50 mg, 0.16 mM) and the suspension stirred under argon atmosphere for 30 minutes. Tetrakis (triphenyl phosphine) palladium (O) (25 mg, 0.02 mM) was added rapidly. The reaction mixture was heated to 80° C. and agitated at that temperature under an argon atmosphere for 16 hours and allowed to cool to room temperature. When the mixture had reached room temperature, a saturated solution of ammonium acetate (5 mL) was added and the mixture agitated at room temperature for 30 minutes. DME (5 mL) was added and the mixture was agitated for an additional 30 minutes, then transferred to a fritted filter funnel and washed sequentially with distilled water, DMF, distilled water, 2 N HCl, distilled water, DMF, distilled water, methanol, DCM and methanol (50 mL of each which was allowed to equilibrate for 10 minutes between washes). Product was dried under vacuum to produce Tagged Wang #1.

2. Tagged Wang #2

Wang iodopolystyrene synthesized as described in Example 1 (100 mg) was dissolved in a solvent mixture of DMF/distilled water/TEA (9:1:1) (5 mL) and allowed to swell for 30 minutes at room temperature. A premixed solution of DMF (0.5 mL) containing 5-cyano-1-pentyne (100 mg, 1.07 mM) and 2-methoxy-5-cyano-phenylacetylene (25 mg, 0.16 mM) was added to the polymer bead suspension followed by potassium carbonate (50 mg, 0.36 mm), tetrabutylammonium bromide (50 mg, 0.16 mM) and the suspension stirred under argon atmosphere for 30 minutes. Tetrakis (triphenylphosphine) palladium (O) (25 mg, 0.02 mM) was added rapidly. The reaction mixture was heated to 80° C. and agitated at that temperature under an argon atmosphere for 16 hours and allowed to cool to room temperature. When the mixture had reached room temperature, a saturated solution of ammonium acetate (5 mL) was added and the mixture agitated at room temperature for 30 minutes. Dimethoxyethane (5 mL) was added and the mixture was agitated for an additional 30 minutes, then transferred to a fritted filter funnel and washed sequentially with distilled water, DMF, distilled water, 2 N HCl, distilled water, DMF, distilled water, methanol, DCM and methanol (50 mL of each which was allowed to equilibrate for 10 minutes between washes). Product was dried under vacuum to produce Tagged Wang #2.

3. Tagged Wang #3

Wang iodopolystyrene synthesized as described in Example 1 (100 mg) was dissolved in a solvent mixture of DMF/distilled water/TEA (9:1:1) (5 mL) and allowed to swell for 30 minutes at room temperature. A premixed solution of DMF (0.5 mL) containing 5-cyano-1-pentyne (100 mg, 1.07 mM) and 6-methoxy-6-paracyanophenyl-6-methyl-1-hexyne (50 mg, 0.22 mM) was added to the polymer bead suspension followed by potassium carbonate (50 mg, 0.36 mm), tetrabutylammonium bromide (50 mg, 0.16 mM) and the suspension stirred under argon atmosphere for 30 minutes. Tetrakis(triphenylphosphine)palladium(O) (25 mg, 0.02 mM) was added rapidly. The reaction mixture was heated to 80° C. and agitated at that temperature under an argon atmosphere for 16 hours and allowed to cool to room temperature. When the mixture had reached room temperature, a saturated solution of ammonium acetate (5 mL) was added and the mixture agitated at room temperature for 30 minutes. DME (5 mL) was added and the mixture was agitated for an additional 30 minutes, then transferred to a fritted filter funnel and washed sequentially with distilled water, DMF, distilled water, 2 N HCl, distilled water, DMF, distilled water, methanol, DCM and methanol (50 mL of each which was allowed to equilibrate for 10 minutes between washes). Product was dried under vacuum to produce Tagged Wang #3.

4. Tagged Wang #4

Wang iodopolystyrene synthesized as described in Example 1 (100 mg) was dissolved in a solvent mixture of DMF/distilled water/TEA (9:1:1) (5 mL) and allowed to swell for 30 minutes at room temperature. A premixed solution of DMF (0.5 mL) containing 5-cyano-1-pentyne (100 mg, 1.07 mM) and 6-methoxy-6-paracyanophenyl-6-methyl-1-hexyne (12.5 mg, 0.06 mM) was added to the polymer bead suspension followed by potassium carbonate (50 mg, 0.36 mm), tetrabutylammonium bromide (50 mg, 0.16 mM) and the suspension stirred under argon atmosphere for 30 minutes. Tetrakis (triphenylphosphine) palladium (O) (25 mg, 0.02 mM) was added rapidly. The reaction mixture was heated to 80° C. and agitated at that temperature under an argon atmosphere for 16 hours and allowed to cool to room temperature. When the mixture had reached room temperature, a saturated solution of ammonium acetate (5 mL) was added and the mixture agitated at room temperature for 30 minutes. DME (5 mL) was added and the mixture was agitated for an additional 30 minutes, then transferred to a fritted filter funnel and washed sequentially with distilled water, DMF, distilled water, 2 N HCl, distilled water, DMF, distilled water, methanol, DCM and methanol (50 mL of each which was allowed to equilibrate for 10 minutes between washes). Product was dried under vacuum to produce Tagged Wang #4.

B. Attachment of Combinatorial Library to Tagged Wang

The tagged Wang can be used to build the combinatorial library as shown below, wherein $R_2$ can contain different functional groups for attaching additional subunits on each compound.

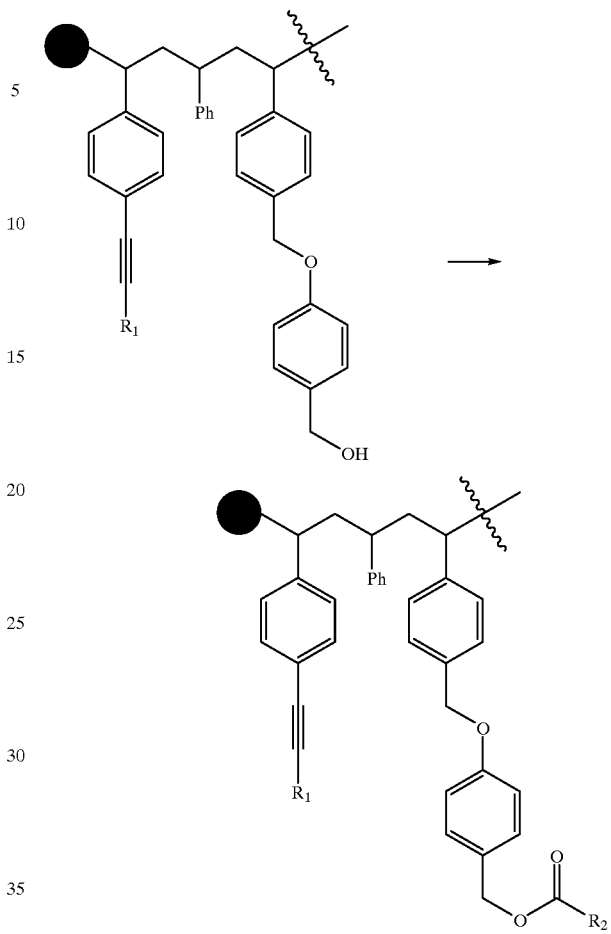

1. Library Member #1

Figure 8:
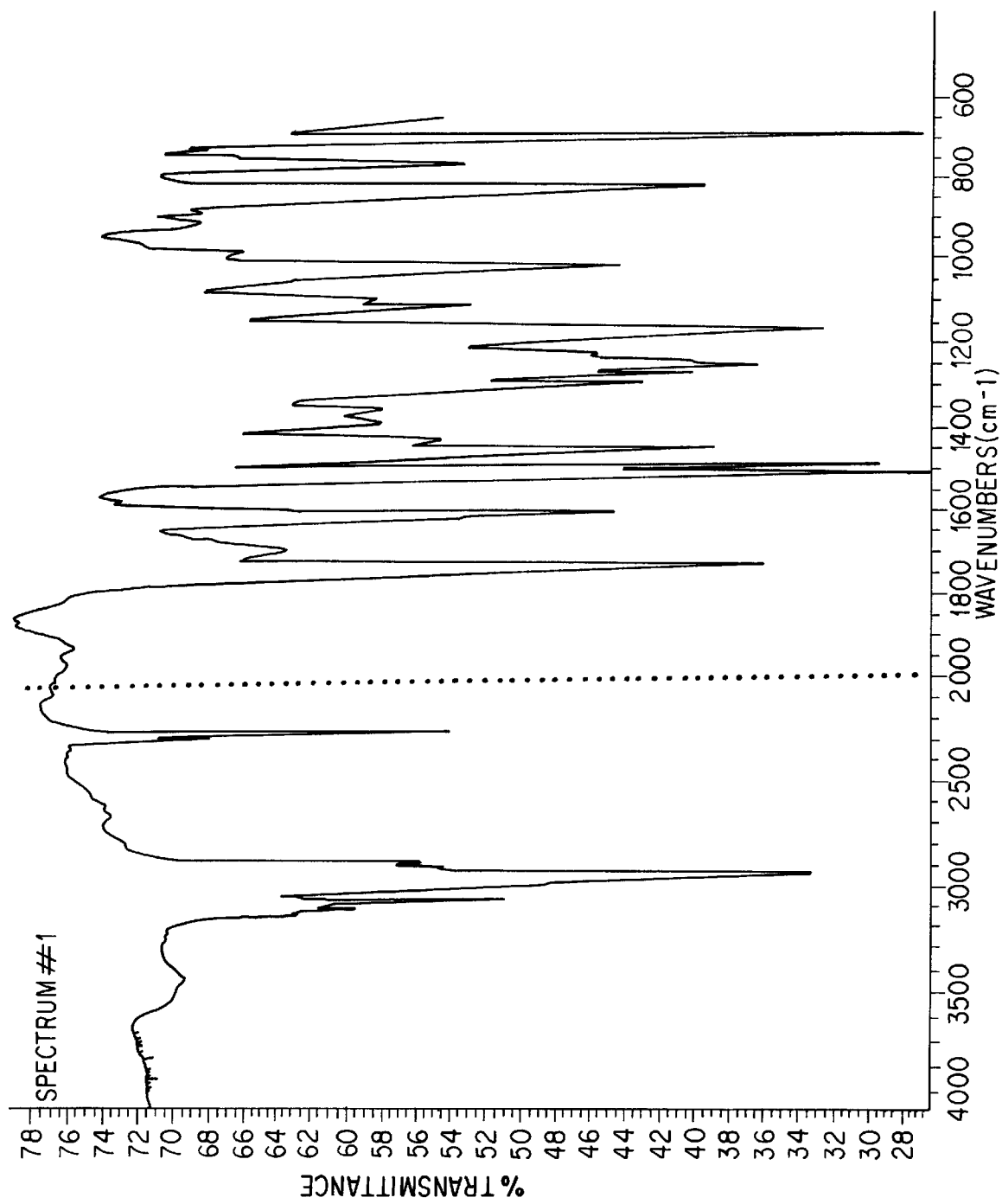
FIG. 8 shows a first FTIR spectrum.

To tagged Wang #1 (5 mg) produced as described above, 1 mL of pyridine and 2 mL of butyric anhydride was added and the mixture stirred at room temperature for 4 hours. The suspension was then transferred to a fritted glass filter funnel and washed sequentially with ethanol, DCM, methanol (10 mL each solvent) and dried under vacuum. A microscope mode fourier transform transflectance infrared (FTIR) spectrum of a single bead from this reaction contained nitrile bands at 2247 and 2226 cm$^{-1}$. See spectrum #1 (FIG. 8).

2. Library Member #2

Figure 9:
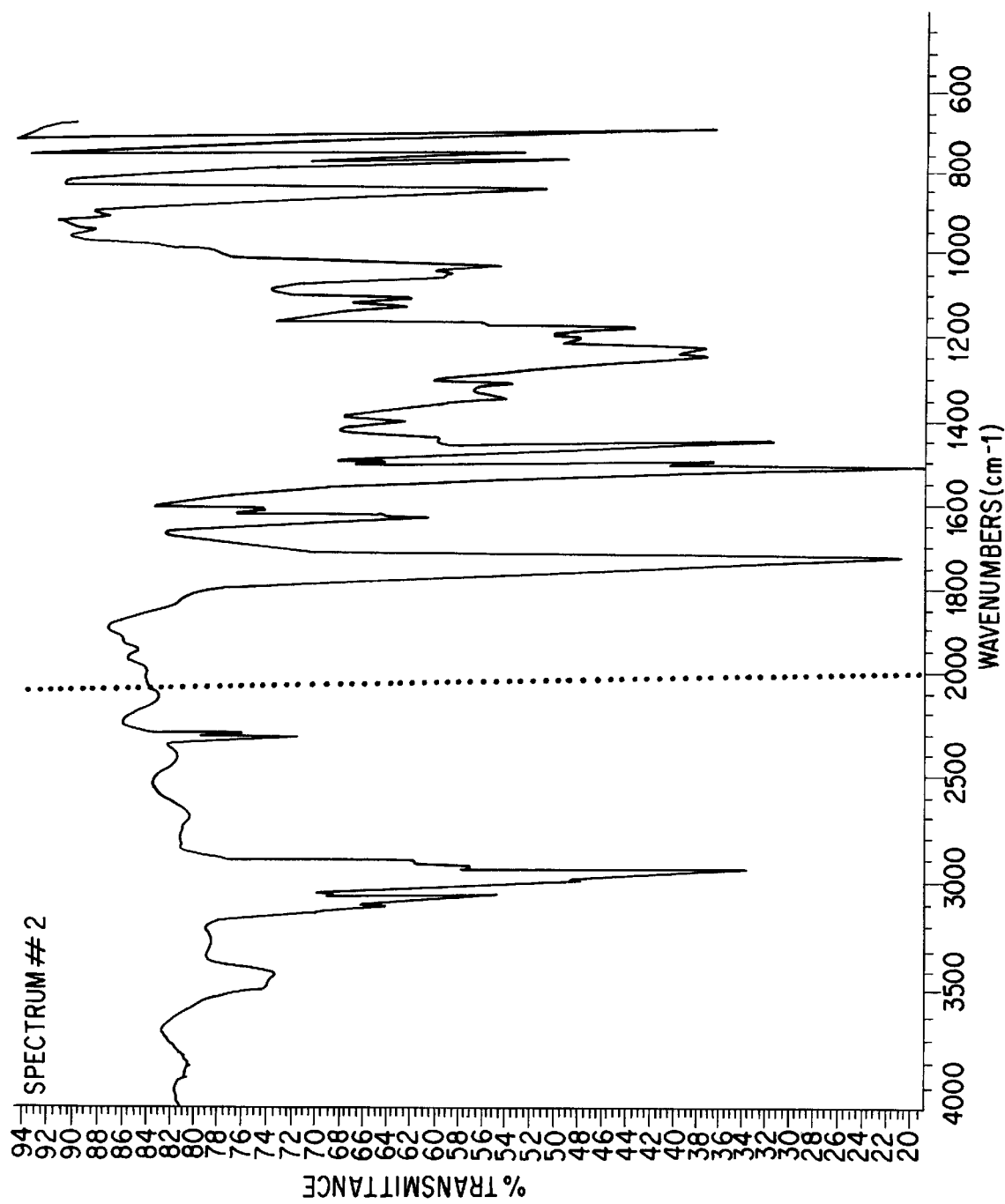
FIG. 9 shows a second FTIR spectrum.

To tagged Wang #2 (5 mg) produced as described above 2 mL of DCM was added and the suspension allowed to swell for 30 minutes. After this time was added n-Fmoc-alanine (20 mg, 0.064 mM) followed by 1,3-diisopropylcarbodiimide (0.2 mL, 0.12 mM) and a catalytic amount of dimethylaminopyridine. The reaction mixture was agitated at room temperature for 6 hours, then transferred to a fritted glass funnel and washed sequentially with DCM, DMF, water, methanol, DCM, methanol (5 mL each solvent) and dried under vacuum. An FTIR spectrum of a single bead from this reaction contained nitrile bands at 2247 and 2226 cm$^{-1}$. See spectrum #2 (FIG. 9).

3. Library Member #3

Figure 10:
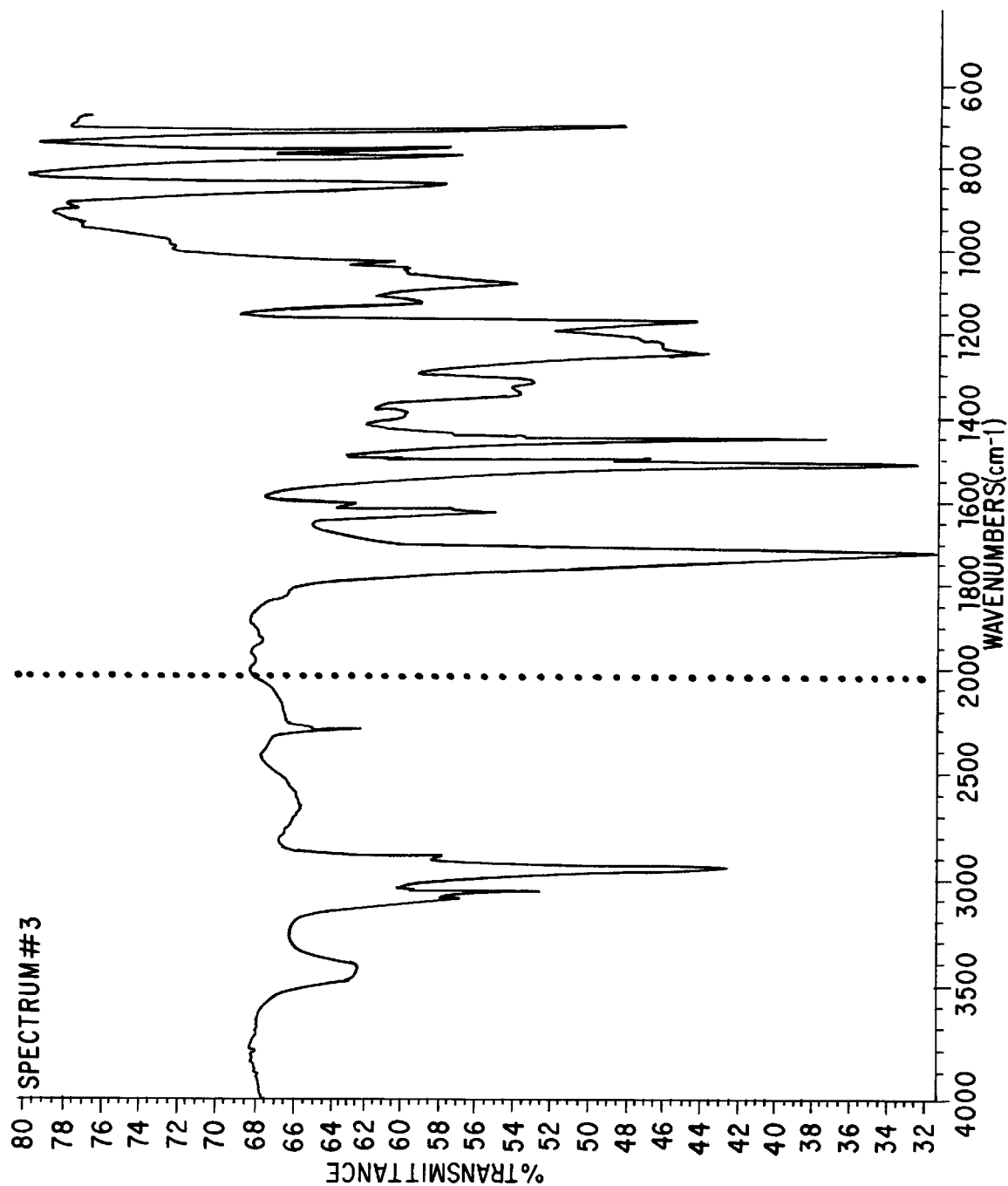
FIG. 10 shows a third FTIR spectrum.

To tagged Wang #3 (5 mg) produced as described above 1 mL of pyridine and 2 mL of acetic anhydride was added and the mixture stirred at room temperature for 4 hours. The suspension was then transferred to a fritted glass filter funnel and washed sequentially with ethanol, DCM, methanol (10 mL each solvent) and dried under vacuum. An FTIR spectrum of a single bead from this reaction contained nitrite bands at 2247 and 2229 cm$^{-1}$. See spectrum #3 (FIG. 10).

4. Library Member #4

Figure 11:
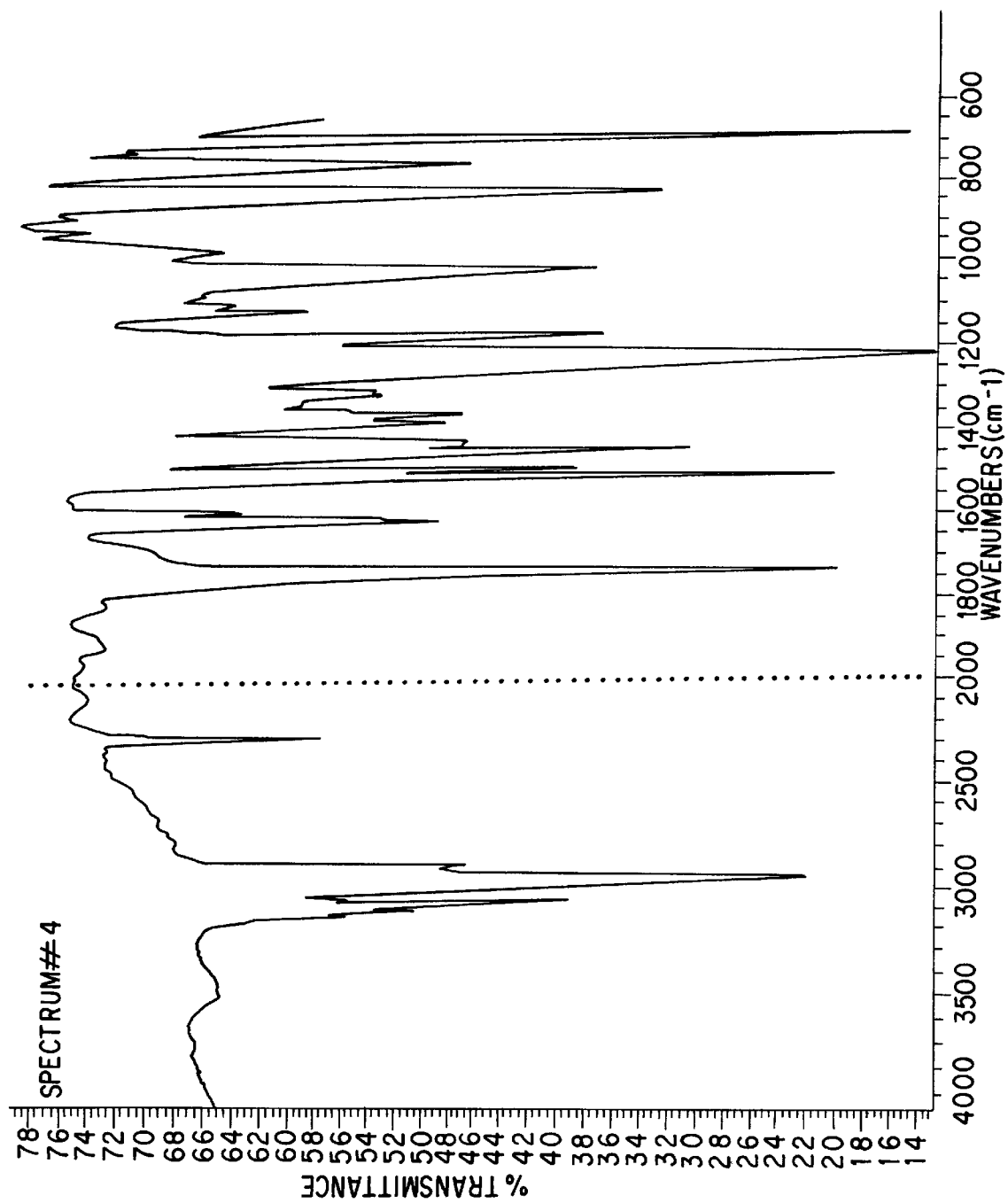
FIG. 11 shows a fourth FTIR spectrum.

To tagged Wang #4 (5 mg) produced as described above 2 mL of DCM was added and the suspension allowed to swell for 30 minutes. After this time was added n-Fmoc-isoleucine (20 mg, 0.056 mM) followed by DIC (0.2 mL, 0.12 mM) and a catalytic amount of DMAP. The reaction mixture was agitated at room temperature for 6 hours, then transferred to a fritted glass funnel and washed sequentially with DCM, DMF, water, methanol, DCM, methanol (5 mL each solvent) and dried under vacuum. An FTIR spectrum of a single bead from this reaction contained nitrile bands at 2247 and 2229 cm$^{-1}$. See spectrum #4 (FIG. 11).

C. Cleavage of Library Members

The tagged Wang can be used to identify the combinatorial library after the library compound is cleaved as shown below.

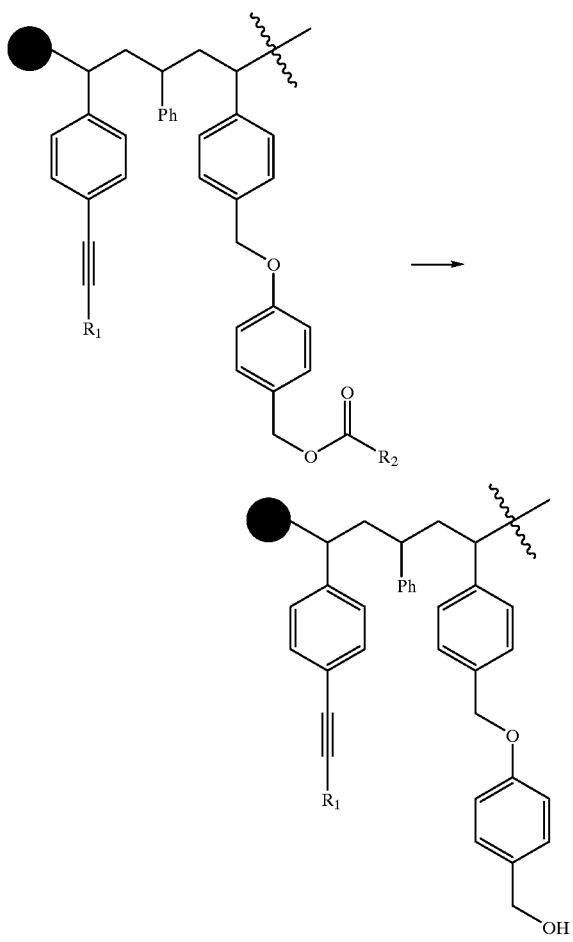

Figure 12:
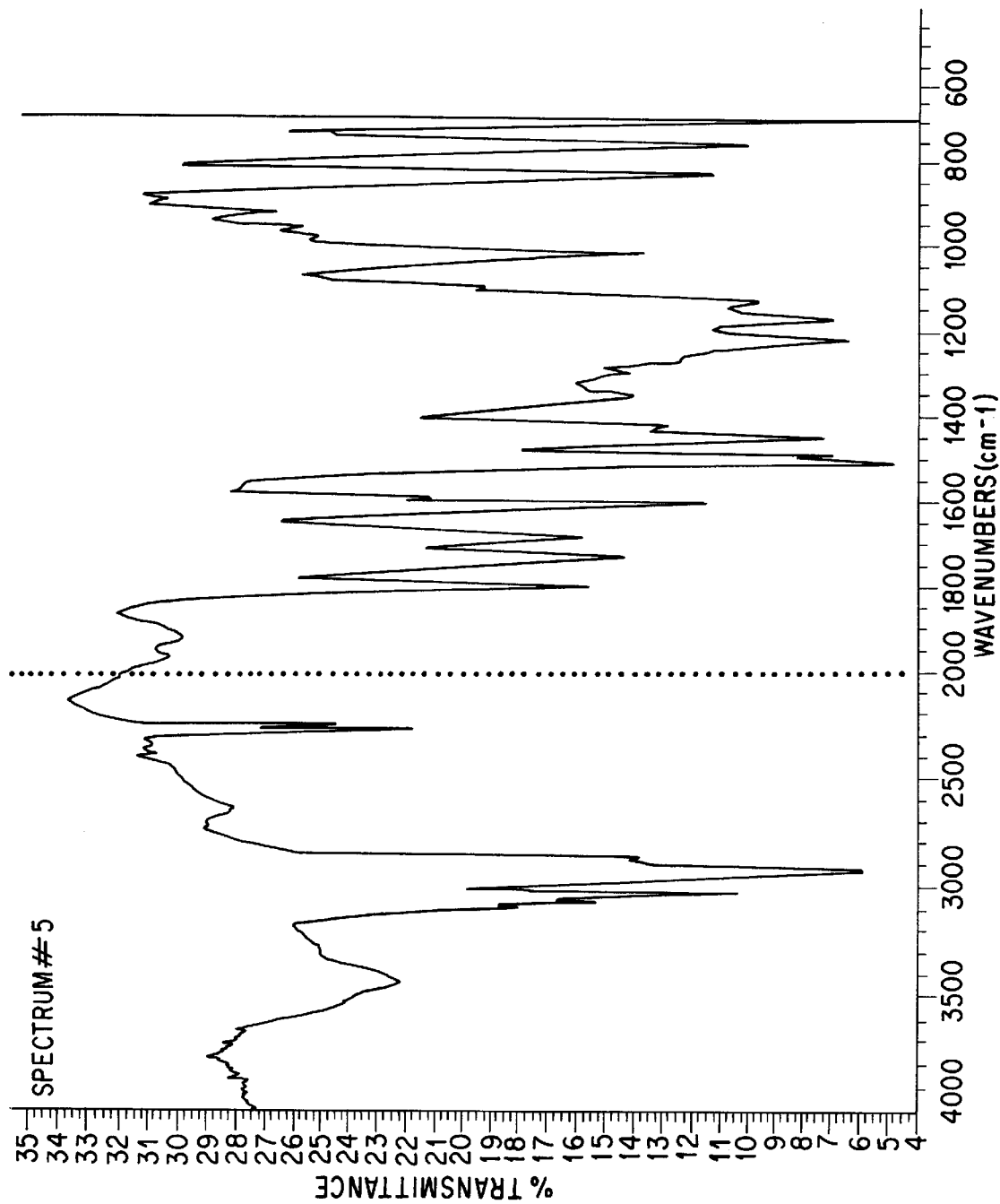
FIG. 12 shows a fifth FTIR spectrum.
Figure 13:
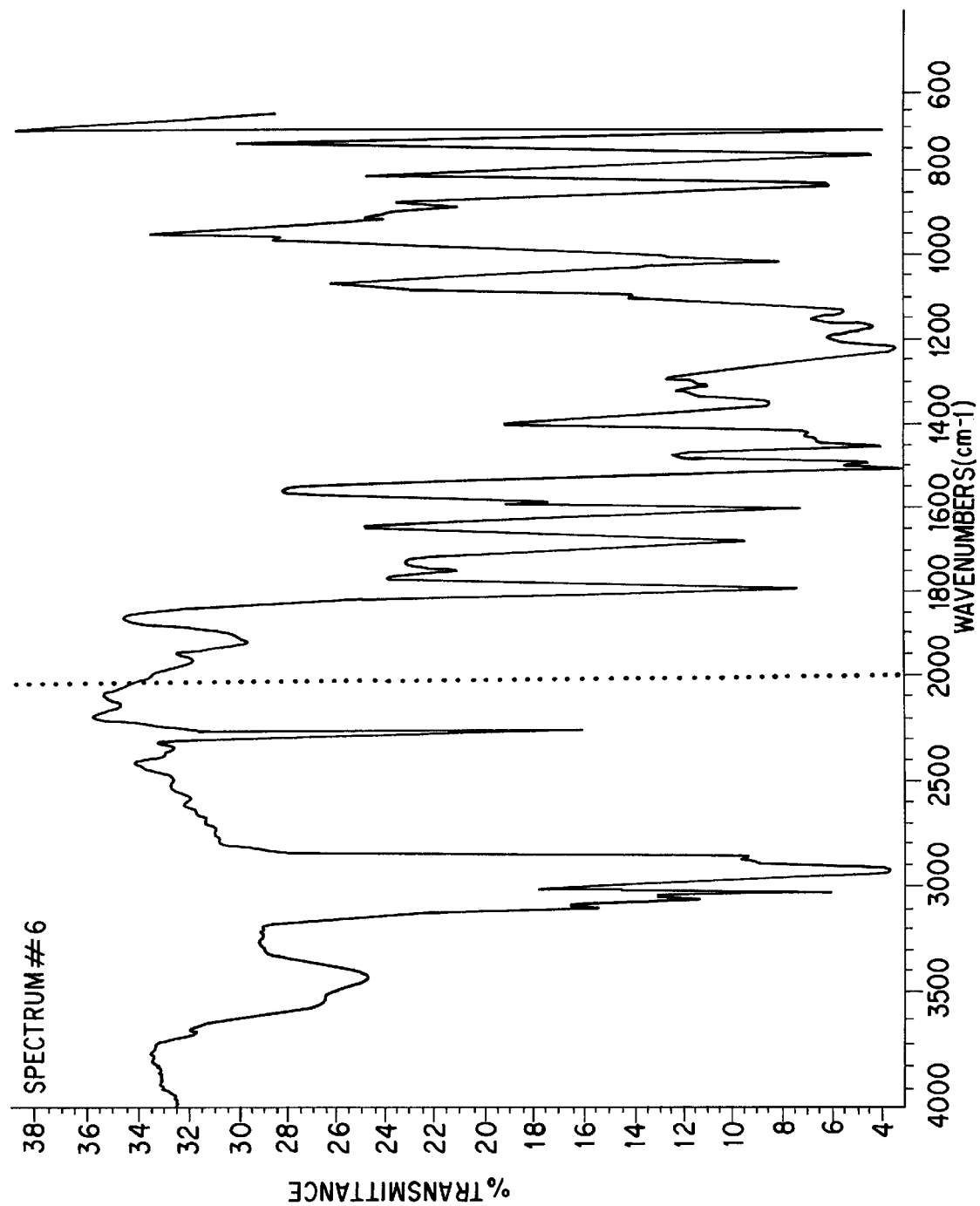
FIG. 13 shows a sixth FTIR spectrum.

1 mg of tagged library from each of the 4 reactions described above (B1–B4) was combined. 1 mL of TFA/distilled water (95:5) was added and the mixture agitated for 30 minutes at room temperature. The mixture was then transferred to a fritted glass filter funnel, washed sequentially with DCM, methanol, water, methanol (5 mL each solvent which was allowed to equilibrate for 15 minutes between washes) and then dried under vacuum. Two individual beads from this cleavage reaction were selected at random and a FTIR spectrum acquired on each bead. A comparison of these FTIR spectra with the spectra obtained from library members #1–4 (B1–B4 above) clearly showed the two beads had belonged to respectively; library #2 and #4. See spectra #'s 5 (FIG. 12) and 6 (FIG. 13).

Example 3
Raman Spectroscopy Coding
Synthesis of Raman Tagged Wang
1,5-decadiyne Wang iodopolystyrene (100 mg), synthesized as described in Example 1, was dissolved in a solvent mixture of DMF/distilled water/TEA (9:1:1) (5 mL) and allowed to swell for 30 minutes at room temperature. 1,5-decadiyne (100 mg) in DMF (2 mL) was added to the polymer bead suspension. Potassium carbonate (50 mg, 0.36 mm) and tetrabutylammonium bromide (50 mg, 0.16 mM) were then added and the suspension was stirred under argon atmosphere for 30 minutes. Tetrakis (triphenylphosphine) palladium (O) (25 mg, 0.02 mM) was added rapidly. The reaction mixture was heated to 80° C. and agitated at that temperature under an argon atmosphere for 16 hours and allowed to cool to room temperature. When the mixture had reached room temperature, a saturated solution of ammonium acetate (5 mL) was added and the mixture agitated at room temperature for 30 minutes. DME (5 mL) was added and the mixture was agitated for an additional 30 minutes, transferred to a fritted filter funnel and washed sequentially with distilled water, DMF, distilled water, 2 N HCl, distilled water, DMF, distilled water, methanol, DCM and methanol (50 mL of each which was allowed to equilibrate for 10 minutes between washes). The product was dried under vacuum to produce a tagged bead containing only one Raman active acetylene tag.

Example 4
Raman Spectroscopy Coding of Aminopolystyrene Resin
Synthesis of Raman Tagged Aminopolystyrene
10,12-tricosadiynoic Acid Aminopolystyrene resin (100 mg) was dissolved in DCM (dried by distillation off from calcium hydride) and allowed to swell for 15 minutes. 10,12-tricosadiynoic acid (50 mg, 0.12 mM), DIC (30 mg, 0.24 mM) and a catalytic amount (<1 mg) of DMAP were added and the mixture agitated for 16 hours at room temperature. The resin was transferred to a fritted funnel and washed sequentially with dimethylformamide, water, methanol, DCM, methanol (30 mL of each solvent allowing 15 minutes soak each solvent to swell and equilibrate).

10,12-heptacosadiynoic Acid

The procedure above was also used to attach 10,12-heptacosadiynoic acid.

Example 5
Synthesis of Raman Coded or Ratio Coded Lysine Polystyrene
Lysine Tag Linker Resin Synthesis Aminomethylpolystyrene (100 mg, 1.2 mM/g) was swelled in DCM for 30 minutes and to this suspension was added successively N-α-Boc-N-ε-Fmoc lysine (115 mg, 2 eq.), N,N-diisoproplyethylamine (55 mL, 4 eq.), PyBroP (74 mg, 2 eq.) and the reaction mixture aggitated for 4 hrs. at room temperature. After this time the reaction mixture was transfered to a fritted funnel and washed sequentially with 5 ml each of: DCM, methanol, DMF, water, and methanol then dryed under vacuum.

The resultant N-alpha-Boc-N-epsilon-Fmoc lysine aminopolystyrene was Fmoc deprotected by aggitation with 20% piperidine in DMF for 30 minuted, then transfered to a fritted funnel and washed sequentially with 5 ml each of: DCM, methanol, DMF, water, and methanol then dryed under vacuum.

Phenylpropiolic Acid, 10,12-tricosadiynoic Acid—Molar Ratio (1:1 Tags 4 & 7)

Figure 14:
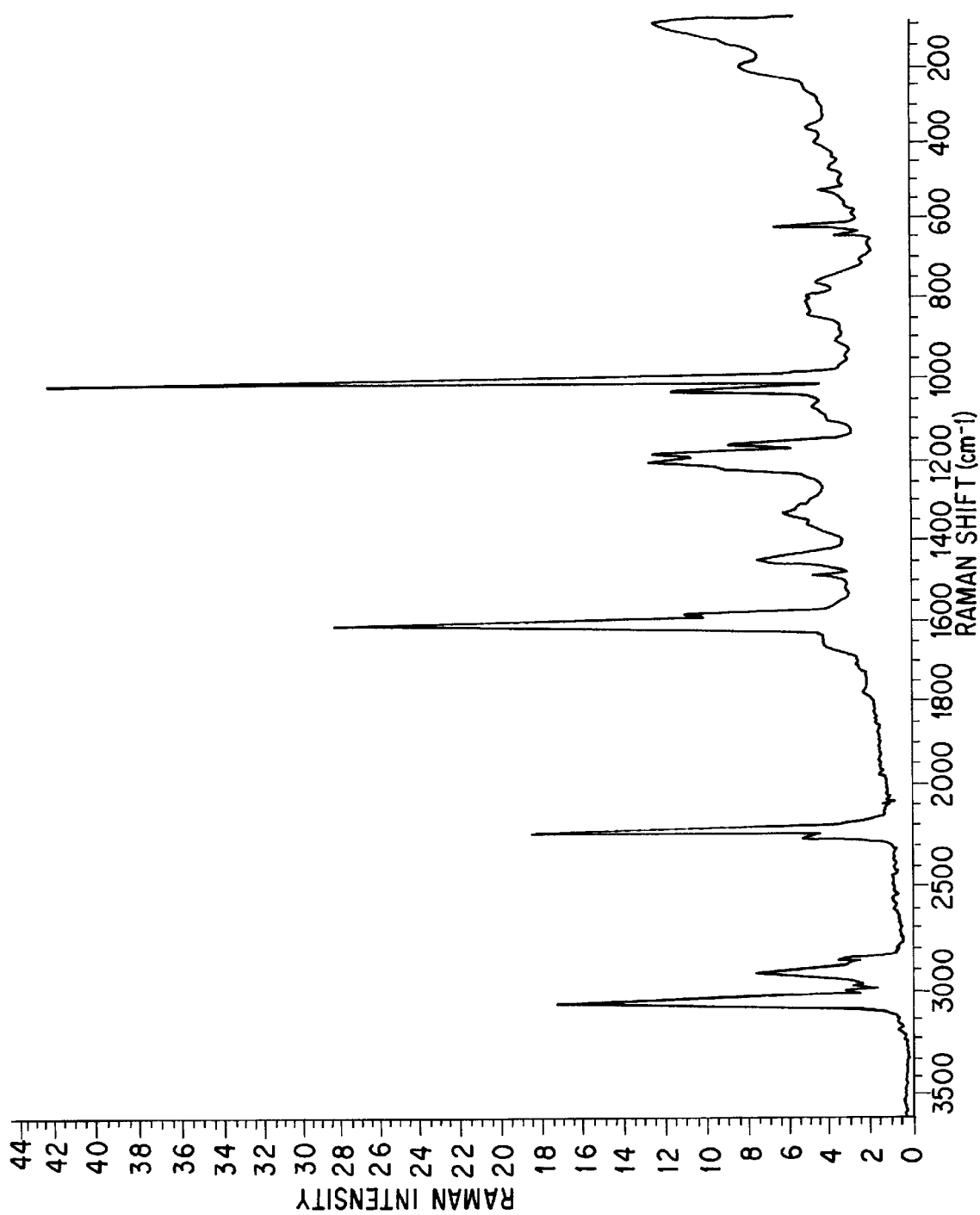
FIG. 14 shows a Raman spectrum.

The resultant N-alpha-Boc-lysine aminopolystyrene was swelled in DCM for 30 minutes and to this suspension was added a mixture phenylpropiolic acid (35 mg, 2 eq., tag 4), 10,12-tricosadiynoic acid (83 mg, 2 eq., tag 7) of DIC (55 mL, 4 eq.), PyBroP (74 mg, 2 eq.) and the reaction mixture aggitated for 4 hrs. at room temperature. After this time the reaction mixture was transferred to a fritted funnel and washed sequentially with 5 ml each of: DCM, methanol, DMF, water then dryed under vacuum. This proceedure thus generated coded, protected lysine aminopolystyrene available for library attachment. Spectrum #7 (FIG. 14) is a Raman spectrum of this entity.

Phenylpropiolic Acid, 10,12-tricosadiynoic Acid—Molar Ratio (1.4 Tags 4 & 7)

Aminomethylpolystyrene (100 mg, 1.2 mM/g) was swelled in DCM for 30 minutes and to this suspension was added successively N-α-Boc-N-ε-Fmoc lysine (115 mg, 2 eq.), DIC (55 mL, 4 eq.), PyBroP (74 mg, 2 eq.) and the reaction mixture aggitated for 4 hrs. at room temperature. After this time the reaction mixture was transferred to a fritted funnel and washed sequentially with 5 ml each of: DCM, methanol, DMF, water, and methanol then dryed under vacuum.

The resultant N-alpha-Boc-N-epsilon-Fmoc lysine aminopolystyrene was Fmoc deprotected by aggitation with 20% piperidine in DMF for 30 minutes, then transfered to a fritted funnel and washed sequentially with 5 ml each of: DCM, methanol, DMF, water, and methanol then dryed under vacuum.

Figure 15:
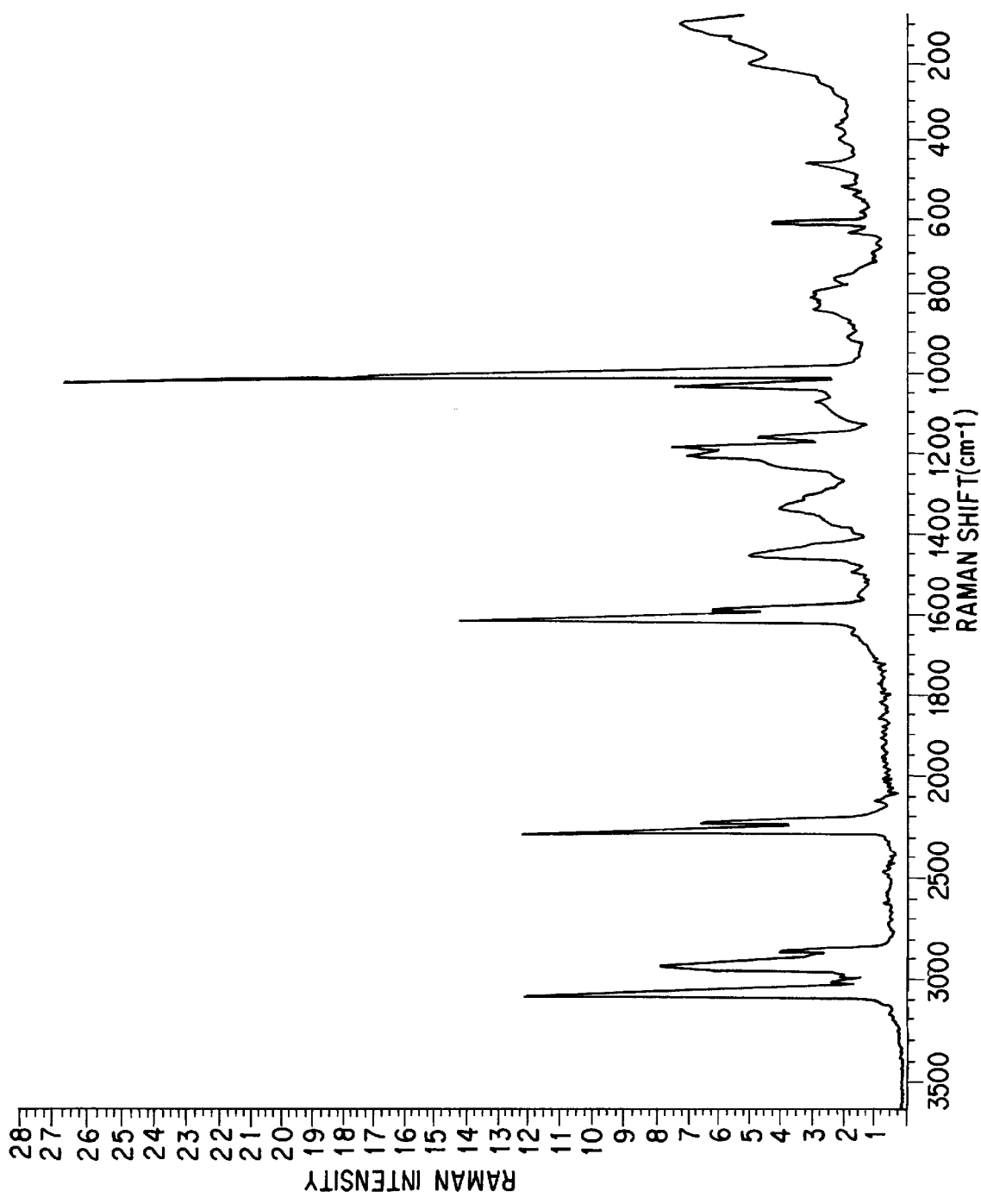
FIG. 15 shows a Raman spectrum.

The resultant N-alpha-Boc-lysine aminopolystyrene was swelled in DCM for 30 minutes and to this suspension was added a mixture of phenylpropiolic acid (16 mg, 1 eq., tag 4), 10,12-tricosadiynoic acid (166 mg, 4 eq., tag 7), DIC (55 mL, 4 eq.), PrBrop (74 mg, 2 eq.) and the reaction mixture aggitated for 4 hrs. at room temperature. After this time the reaction mixture was transferred to a fritted funnel and washed sequentially with 5 ml each of: DCM, methanol, DMF, water, and methanol then dryed under vacuum. This proceedure thus generated coded, protected lysine aminopolystyrene available for library attachment. Spectrum #8 (FIG. 15) is a Raman spectrum of this entity.

Weight Ratio (1:2 Tags 4 & 7)

The N-alpha-Boc-lysine aminopolystyrene described above was swelled in DCM for 30 minutes and to this suspension was added phenylpropiolytic acid (Tag #4, 50 mg), 10,12-tricosadiynoic acid (Tag #7, 100 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment.

Weight Ratio (1:4 Tags 4 & 7)

Figure 16:
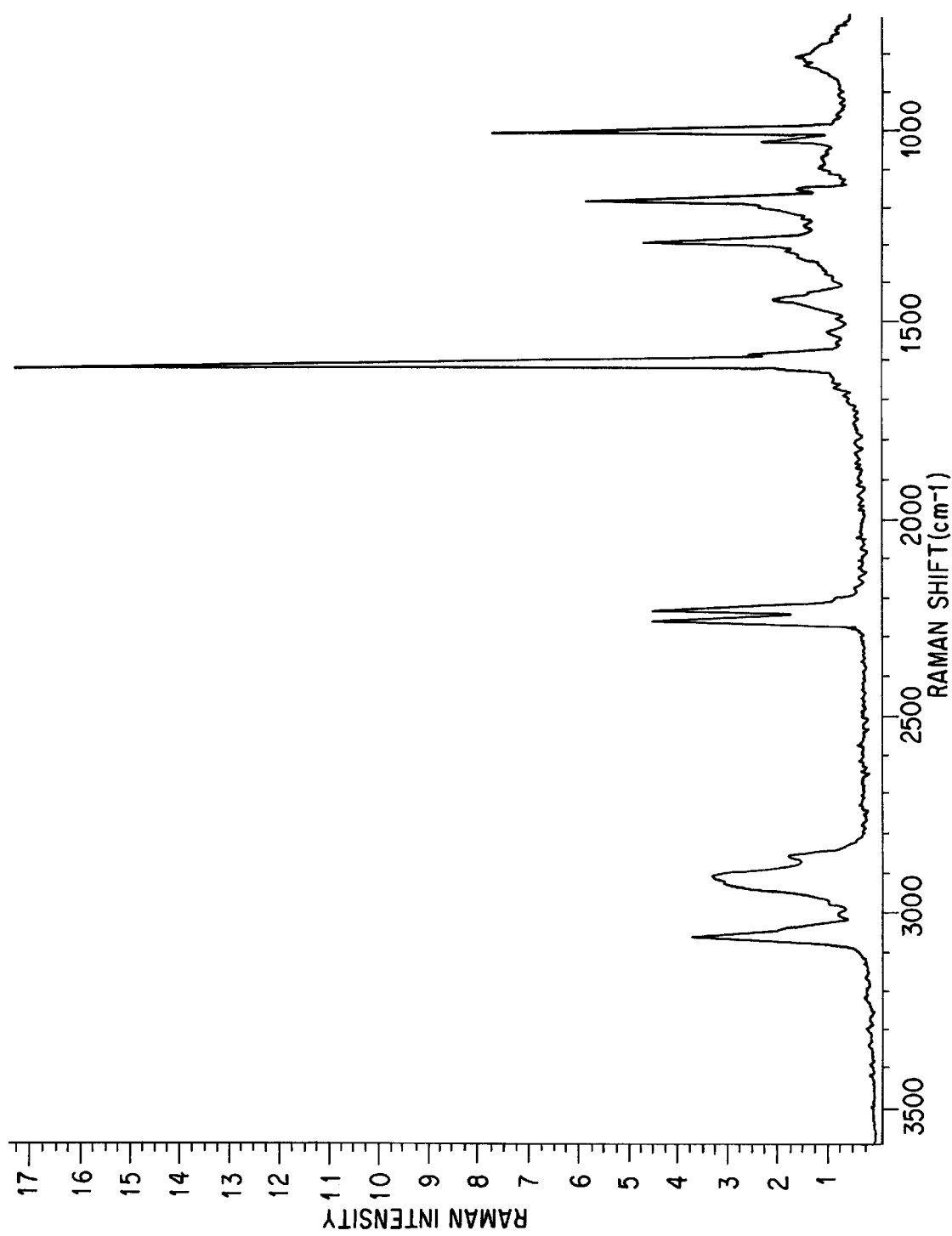
FIG. 16 shows a Raman spectrum.

The N-alpha-Boc-lysine aminopolystyrene described above was swelled in DCM for 30 minutes and to this suspension was added phenylpropiolytic acid (Tag #4, 25 mg), 10,12-tricosadiynoic acid (Tag #7, 100 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment. FIG. 16 is a Raman spectrum of this entity. This example demonstrates that ratio does not necessarily mean equivalence. Weight ratios can also be used.

Weight Ratio (1:10 Tags 2 & 7)

The N-alpha-Boc-lysine aminopolystyrene described above was swelled in DCM for 30 minutes and to this suspension was added p-(phenylethynyl)-benzoic acid (Tag #2, 10 mg), 10,12-tricosadiynoic acid (Tag #7, 100 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment.

Weight Ratio (1:1 Tags 4 & 6)

The N-alpha-Boc-lysine aminopolystyrene described above was swelled in DCM for 30 minutes and to this suspension was added phenylpropiolytic acid (Tag #4, 50 mg), 2-(pyrimidine)dodec-10-ynoic acid (Tag #6, 50 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment.

Weight Ratio (1:4 Tags 4 & 6)

The N-alpha-Boc-lysine aminopolystyrene described above was swelled in DCM for 30 minutes and to this suspension was added phenylpropiolytic acid (Tag #4, 25 mg), 2-(pyrimidine)dodec-10-ynoic acid (Tag #6, 100 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment.

p-(4'-methoxyphenylethynyl)benzoic Acid Tagged Resin (Tag 1)

Figure 17:
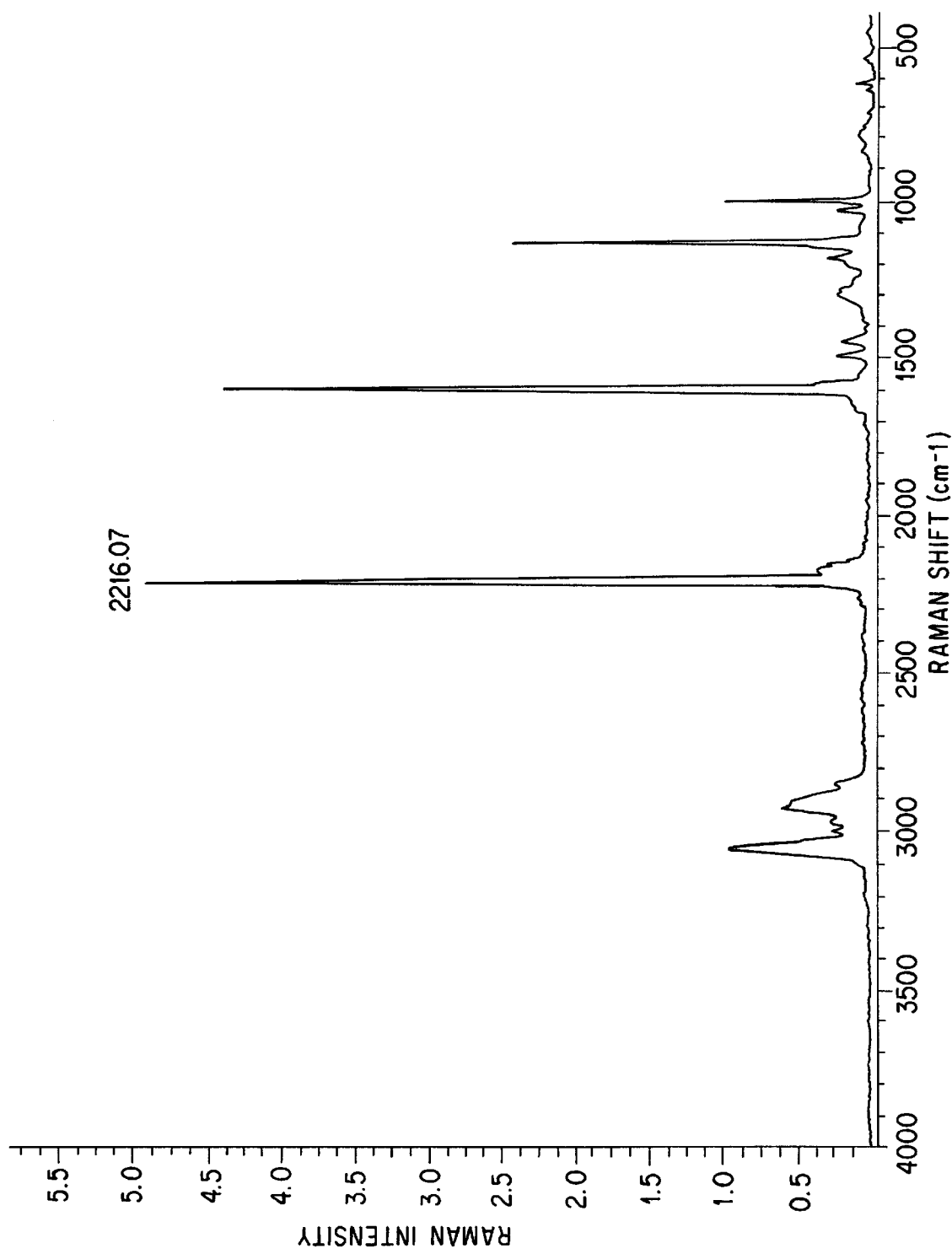
FIG. 17 shows a Raman spectrum.

The N-alpha-Boc-lysine aminopolystyrene described above was swelled in DCM for 30 minutes and to this suspension was added p-(4'-methoxyphenyl-ethynyl)benzoic acid (Tag #1, 100 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment. FIG. 17 provides its Raman spectrum.

p-(phenylethynyl)benzoic Acid Tagged Resin (Tag 2)

Figure 18:
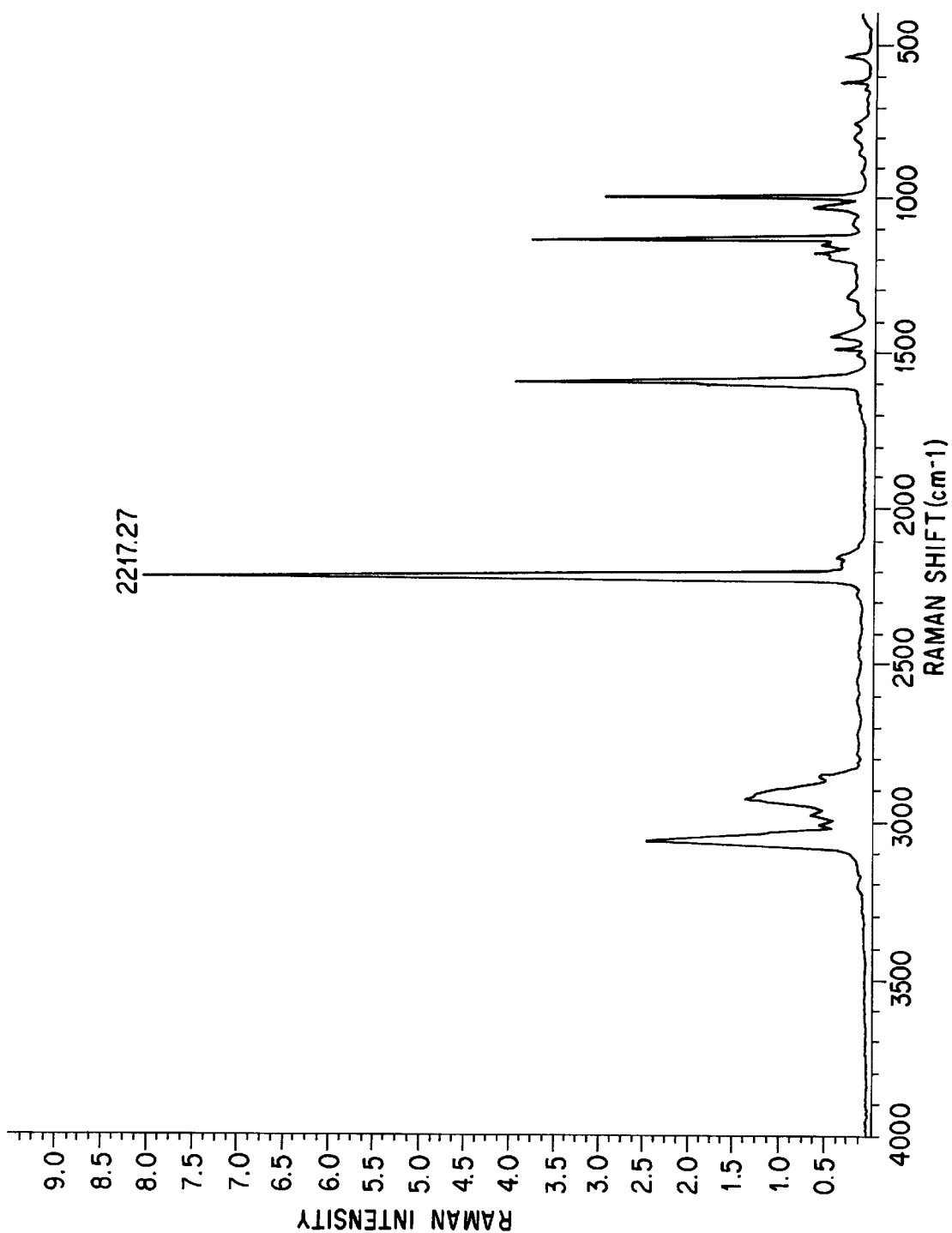
FIG. 18 shows a Raman spectrum.

The N-alpha-Boc-lysine aminopolystyrene described above was swelled in DCM for 30 minutes and to this suspension was added p-(phenylethynyl)-benzoic acid (tag #2, 100 mg), DIC (55 mL, 4 eq.), PyBroP (74 mg, 2 eq.) and the reaction mixture aggitated for 12 hrs. at room temperature. After this time the reaction mixture was transferred to a fritted funnel and washed sequentially with 5 ml each of: DCM, methanol, DMF, water, and methanol the dryed under vacuum. This proceedure thus generated coded, protected lysine aminopolystyrene available for library attachment. FIG. 18 provides its Raman spectrum.

p-(4'-fluorophenylethynyl)benzoic Acid Tagged Resin (Tag 3)

Figure 19:
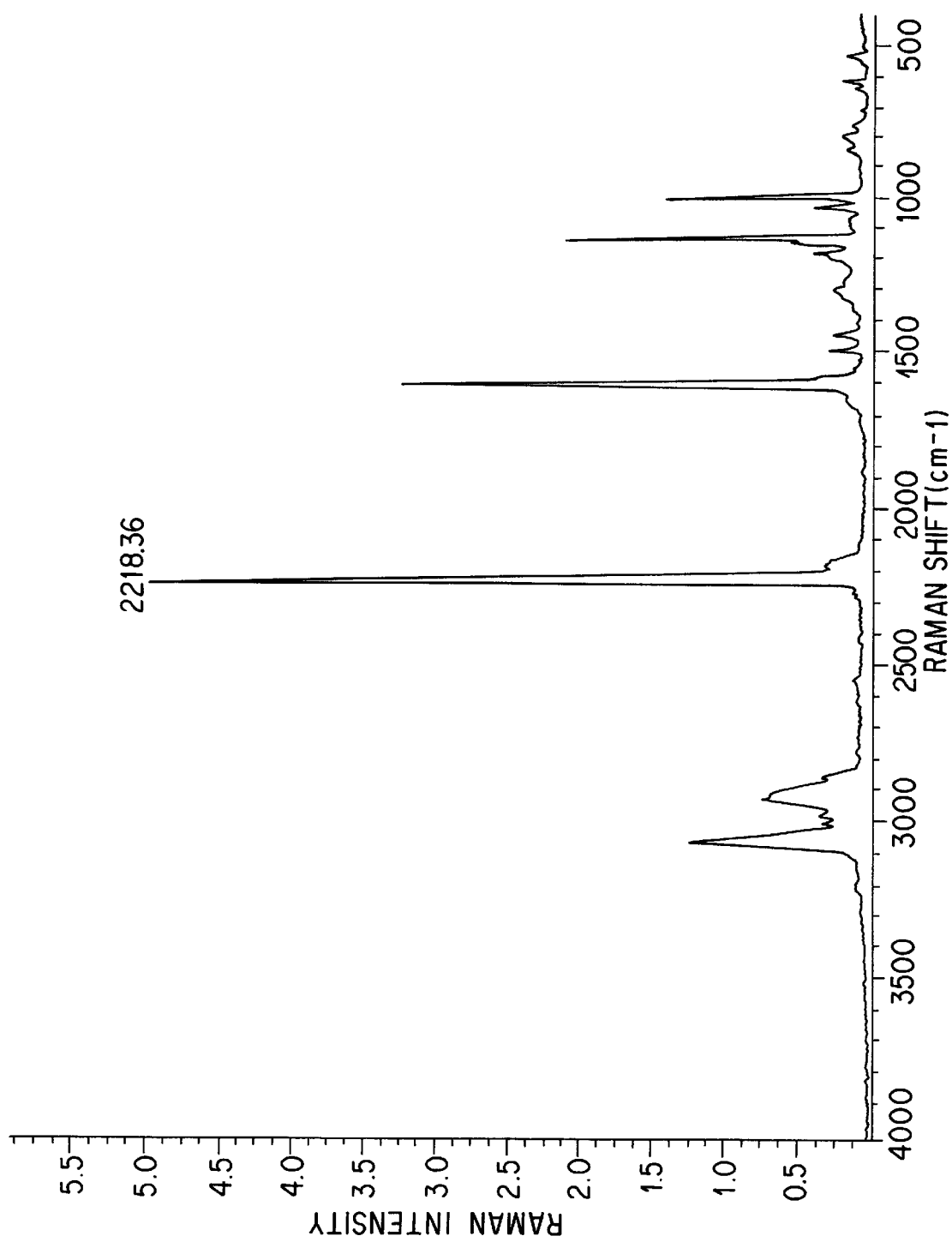
FIG. 19 shows a Raman spectrum.

The N-alpha-Boc-lysine aminopolystyrene described above was swelled in DCM for 30 minutes and to this suspension was added p-(4'-fluorophenyl-ethynyl)benzoic acid (Tag #3, 100 mg), DIC (55 mL, 4 eq.), PyBroP (74 mg, 2 eq.) and the reaction mixture aggitated for 12 hrs. at room temperature. After this time the reaction mixture was transfered to a fritted funnel and washed sequentially with 5 ml each of: DCM, methanol, DMF, water, and methanol the dryed under vacuum. This proceedure thus generated coded, protected lysine aminopolystyrene available for library attachment. FIG. 19 provides its Raman spectrum.

27

Phenylpropiolic Acid Tagged Resin (Tag 4)

The N-alpha-Boc-lysine aminopolystyrene described above was swelled in DCM for 30 minutes and to this suspension was added phenylpropiolic (Tag #4, 100 mg), DIC (55 mL, 4 eq.), PyBroP (74 mg, 2 eq.) and the reaction mixture aggitated for 12 hrs. at room temperature. After this time the reaction mixture was transfered to a fritted funnel and washed sequentially with 5 ml each of: DCM, methanol, DMF, water, and methanol the dryed under vacuum. This proceedure thus generated coded, protected lysine aminopolystyrene available for library attachment.

2-(thiazolyl)dodec-10-ynoic Acid Tagged Resin (Tag 5)

The N-alpha-Boc-lysine aminopolystyrene described above was swelled in DCM for 30 minutes and to this suspension was added 2-(thiazolyl)dodec-10-ynoic acid (Tag #5, 100 mg), DIC (55 mL, 4 eq.), PyBroP (74 mg, 2 eq.) and the reaction mixture aggitated for 12 hrs. at room temperature. After this time the reaction mixture was transfered to a fritted funnel and washed sequentially with 5 ml each of: DCM, methanol, DMF, water, and methanol the dryed under vacuum. This proceedure thus generated coded, protected lysine aminopolystyrene available for library attachment.

2-(pyrimidine)dodec-10-ynoic Acid Tagged Resin (Tag 6)

The N-alpha-Boc-lysine aminopolystyrene described above was swelled in DCM for 30 minutes and to this suspension was added 2-(pyrimidine)dodec-10-ynoic acid (Tag #6, 100 mg), DIC (55 mL, 4 eq.), PyBroP (74 mg, 2 eq.) and the reaction mixture aggitated for 12 hrs. at room temperature. After this time the reaction mixture was transfered to a fritted funnel and washed sequentially with 5 ml each of: DCM, methanol, DMF, water, and methanol the dryed under vacuum. This proceedure thus generated coded, protected lysine aminopolystyrene available for library attachment.

10,12-tricosadiynoic Acid Tagged Resin (Tag 7)

The N-alpha-Boc-lysine aminopolystyrene described above was swelled in DCM for 30 minutes and to this suspension was added 10,12-tricosadiynoic acid (Tag #7, 100 mg), DIC (55 mL, 4 eq.), PyBroP (74 mg, 2 eq.) and the reaction mixture aggitated for 12 hrs. at room temperature. After this time the reaction mixture was transfered to a fritted funnel and washed sequentially with 5 ml each of: DCM, methanol, DMF, water, and methanol the dryed under vacuum. This proceedure thus generated coded, protected lysine aminopolystyrene available for library attachment.

Additional Tagged Resin

Procedure described above was also used to tag resin with o-biphenyl-non-8-ynoic acid; o-methoxyphenyl-non-8-ynoic acid and o-fluorophenyl-non-8-ynoic acid from Table 1b.

Example 6

Coding of First Step of Synthesis Via Amide Linked Infrared Tags

A. Incorporation of Tags for First Position Tagging on Aminomethyl Polystyrene Resin 1. Loading of Diprotected Lysine onto Aminomethyl Resin

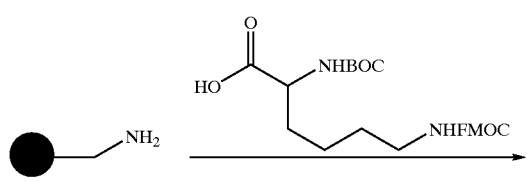

28

-continued

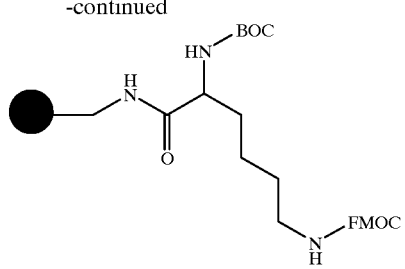

To a suspension of 2.00 g (2.4 mmol) of aminomethyl resin in 30 mL of DCM was added successively 2.25 g (4.8 mmol) of N-alpha-Boc-N-epsilon-Fmoc lysine, 1.69 mL (9.6 mmol) of DIC and 2.24 g (4.8 mmol) of PyBroP. The suspension was rotated at room temperature for 1.5 hours, and drained. The same amounts of reagents were added again to the resin, and the resulting suspension was rotated at room temperature for 1.5 hours. The suspension was drained and the resin was washed successively with five 30-mL portions of DMF and five 30-mL portions of DCM, and dried in vacuo. A 0.65 mmol/g lysine loading was obtained by this procedure, as determined by Fmoc quantitation.

2. Fmoc Deprotection

A 600-mg portion of lysine-loaded resin was divided in 6 pools of 100 mg each. 2 mL of a 20% solution of piperidine in DMF was added to each pool. The resulting suspensions were shaken at room temperature for 10 minutes and drained. The procedure was repeated with shaking over 30 minutes. The suspensions were then drained, washed with seven 5-mL portions of DMF, and dried in vacuo.

3. Attachment of the IR Tags

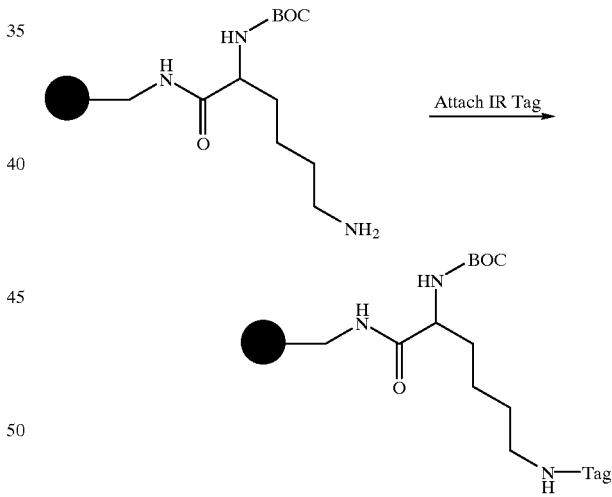

2 mL of DMF, a solution of the desired IR tags (nitrile acids from Table 1, 0.13 mmol) in DMF, 32 mL (0.20 mmol) of DIC, and a catalytic amount of DMAP was added successively to each of the six pools of resin. The mixtures were shaken at room temperature for 16 hours, drained, and the resin in each pool was washed with five 5-mL portions of DMF and five 5-mL portions of DCM, and dried in vacuo. Single-bead FTIR spectra were recorded for each pool and showed appropriate incorporation of the tags.

4. Boc Deprotection 3 mL of a 50% solution of TFA in DCM was added to each of the six pools of tagged resin from step 3 above. The suspensions were shaken at room temperature for 30 minutes, and drained. The procedure was repeated. After draining, the resin in each pool was washed with five 3-mL portions of dichloromethane, five 3-mL portions of 5% diisopropylethylamine in DCM and five 3-mL portions of DCM. The resin was then dried in vacuo.

4-hydroxymethyl Phenoxyacetic Acid Pentafluorophenol Ester Linker

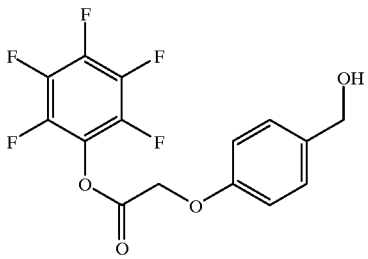

This derivative was prepared according to the procedure described by Atherton et al. (*Tetrahedron*, 1988, 44, 843–857). A solution of 2.22 g (12.08 mmol) of pentafluorophenol in 10 mL of dioxane was added to a solution of 2.00 g (10.98 mmol) of 4-hydroxymethyl phenoxyacetic acid in 20 mL of dry dioxane. The mixture was cooled to 0° C. A solution of 2.49 g (12.08 mmol) of dicyclohexylcarbodiimide in 10 mL of dioxane was added and the mixture was stirred in an ice-bath for 1 hour, at room temperature for 1 hour, and filtered. The filtrate was concentrated in vacuo to afford a white solid. Recrystallization from diethyl ether-hexanes afforded the desired ester as a white solid: mp 114.5–115° C. (lit 111–112° C.).

Attaching the Linker Onto the Six Tagged Resin Pools

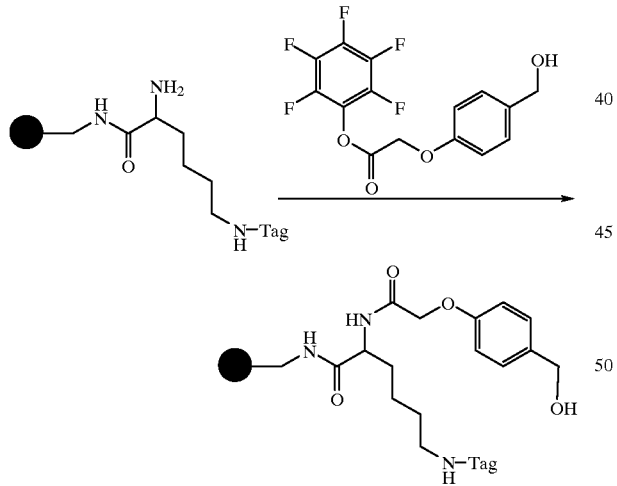

2 mL of DMF and 57 mg (0.20 mmol) of 4-hydroxymethyl phenoxyacetic acid pentafluorophenol ester was added to each of the six pools of tagged resin. The mixtures were shaken at room temperature for 2 hours, and drained. The resins were then washed five 5-mL portions of DMF and five 5-mL portions of DCM, and dried in vacuo.

The process described for six pools above have been used to generate at least 50 unique codes (shown below). However, the ordinary artisan would realize that more combinations and ratios are available for numerous codes.

| Code | Tag(s) | Ratio |
|---|---|---|
| 1 | 2226/2246 | (1:1) |
| 2 | 2226/2246 | (4:1) |
| 3 | 2230/2242 | (1:1) |
| 4 | 2230/2242 | (4:1) |
| 5 | 2230/2246 | (1:1) |
| 6 | 2230/2246 | (1:4) |
| 7 | 2228/2246 | (1:1) |
| 8 | 2228/2246 | (2:1) |
| 9 | 2228/2246 | (4:1) |
| 10 | 2228/2246 | (8:1) |
| 11 | 2232/2246 | (1:1) |
| 12 | 2232/2246 | (2:1) |
| 13 | 2232/2246 | (4:1) |
| 14 | 2232/2246 | (8:1) |
| 15 | 2223/2242 | (1:1) |
| 16 | 2223/2242 | (4:1) |
| 17 | 2223/2242 | (1:4) |
| 18 | 2242 | — |
| 19 | 2223 | — |
| 20 | 2230/2250 | (1:1) |
| 21 | 2230/2250 | (1:2) |
| 22 | 2230/2250 | (1:4) |
| 23 | 2232/2250 | (1:1) |
| 24 | 2232/2250 | (1:2) |
| 25 | 2232/2250 | (1:4) |
| 26 | 2226/2242 | (1:1) |
| 27 | 2226/2242 | (1:2) |
| 28 | 2226/2242 | (2:1) |
| 29 | 2226/2242 | (1:4) |
| 30 | 2226/2242 | (4:1) |
| 31 | 2226/2250 | (2:3) |
| 32 | 2242 | — |
| 33 | 2246 | — |
| 34 | 2228/2242 | (1:1) |
| 35 | 2228/2242 | (1:2) |
| 36 | 2230/2242 | (1:1) |
| 37 | 2230/2242 | (1:4) |
| 38 | 2232/2242 | (1:1) |
| 39 | 2232/2242 | (1:8) |
| 40 | 2220/2242 | (1:1) |
| 41 | 2220/2242 | (1:2) |
| 42 | 2220/2242 | (1:4) |
| 43 | 2220/2242 | (1:8) |
| 44 | 2220/2246 | (1:1) |
| 45 | 2220/2246 | (1:2) |
| 46 | 2220/2246 | (1:8) |
| 47 | 2220 | — |
| 48 | 2226 | — |
| 49 | 2220/2230 | (1:5) |
| 50 | 2220/2230 | (1:10) |

What is claimed is:

1. A process of coding individual members of a combinatorial chemical library synthesized on a plurality of solid supports comprising covalently attaching to each of the solid supports a coding identifier detectable by infrared or Raman spectroscopy, wherein said coding identifier attached to the solid support is detectable by infrared or Raman spectroscopy and said coding identifier is a nitrile.

2. The process of claim 1 wherein the coding identifier is selected from the group consisting of the following structures:

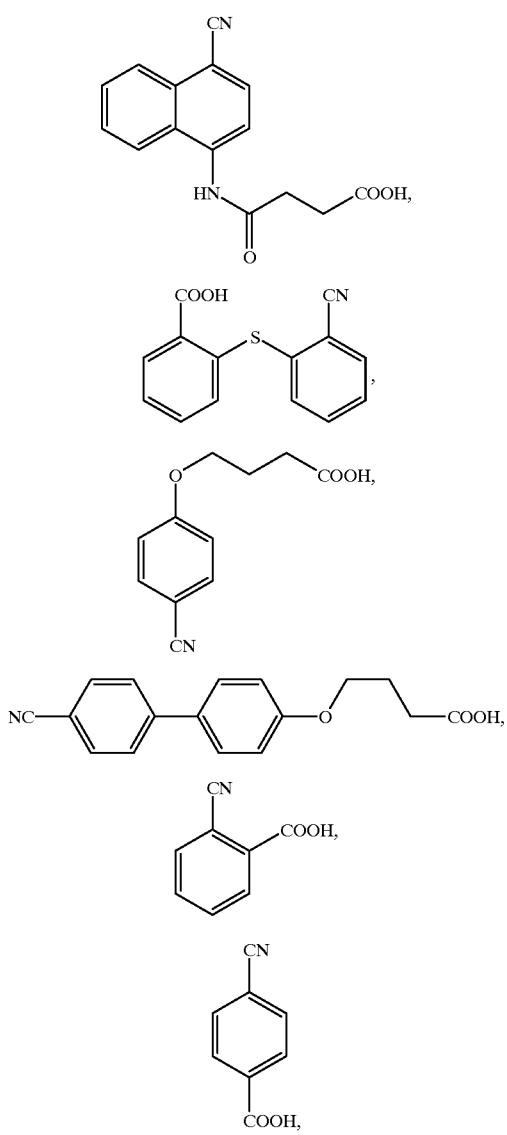
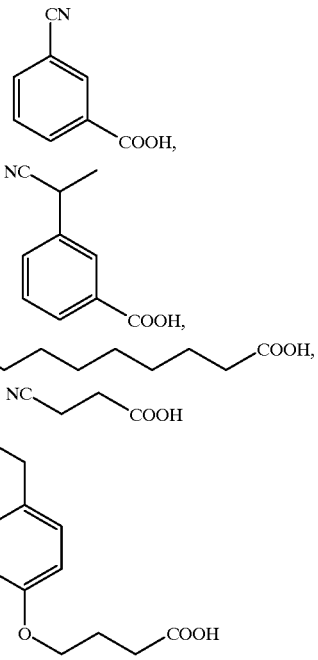
and combinations thereof.
3. The process of claim 1 wherein the coding identifier is covalently attached to the solid supports via a lysine-based linker moiety.
4. The process of claim 3 wherein the lysine-based linker is attached to the solid supports via its alpha amino group and attached to the coding identifier via its epsilon amino group.
* * * * *